United States Patent [19]
King

[11] Patent Number: 6,106,844
[45] Date of Patent: Aug. 22, 2000

[54] IMMUNOMODULATORY PEPTIDES OF VESPID ANTIGEN 5

[75] Inventor: Te Piao King, New York, N.Y.

[73] Assignee: The Rockfeller University, New York, N.Y.

[21] Appl. No.: 09/130,287

[22] Filed: Aug. 6, 1998

Related U.S. Application Data

[62] Division of application No. 08/614,935, Mar. 11, 1996, Pat. No. 5,804,201.

[51] Int. Cl.[7] .......................... A61K 39/35; A61K 39/00; A61K 39/36
[52] U.S. Cl. .................................. 424/275.1; 424/184.1; 424/185.6; 435/69.1; 530/300; 530/806; 530/858; 536/23.2; 536/23.5
[58] Field of Search .............................. 424/275.1, 184.1, 424/185.1; 435/69.1; 530/300, 806, 858; 536/23.2, 23.5

[56] References Cited

FOREIGN PATENT DOCUMENTS

WO 94/20623  9/1994  WIPO .

OTHER PUBLICATIONS

Hoffman, "Hymenoptia Venom Proteins" in National Toxins, R.B. Singh (ed.), Plenum Publishing 6 (1996).
King et al., J. Allergy Clin. Immunol. 98:588–600 (1996).
Müller et al., J. Allergy Clin. Immunol. 97:426 (1996).
Förster et al. (1995) J. Allergy Clin. Immunol. 95:1229–35.
King et al., J. Immunol., 154:577 (1995).
Müller et al., J. Allergy Clin. Immunol. 96:395–402 (1995).
Norman et al., J. Allergy Clin. Immunol. 95:259 (1995).
Briner et al., Proc. Natl. Acad. Sci. U.S.A., 90:7608–12 (1993).
Hoyne et al., J. Exp. Med., 178:1783–1788 (1993).
T.P. King, in "Bronchial Asthma," edited by E.B. Weiss and M. Stein, Little Brown, Boston, pp. 43–49 (1993).
King et al., J. Allergy Clin. Immunol., 91:283 (1993).
Lu et al., J. Immunol. 150:2823 (1993).
P.S. Norman, Current Op. Immunol., 5:968 (1993).
O'Hehir et al., Eruop. J. Clin. Invest., 23:763 (1993).
Mizuku et al., Mammalian Genome, 3:274–280 (1992).
Ales–Martinez, et al., Immunol. Today, 12:201 (1991).
O'Hehir et al., Ann. Rev. Immunol., 9:67 (1991).
Fang et al., Proc. Natl. Acad. Sci., USA, 85:895–899 (1988).
King, J. Allergy Clin. Immunol., 79:113 (1987).
Hoffman, J. Allergy and Clin. Immunol., 75:611 (1985).
King, et al., J. Allergy and Clin. Immunol., 75:621 (1985).

*Primary Examiner*—Michael P. Woodward
*Assistant Examiner*—Mary K Zeman
*Attorney, Agent, or Firm*—Darby & Darby

[57] ABSTRACT

The present invention is directed to immunogenic peptides from vespid antigen 5. These immunogenic peptides can be used in immunotherapy for vespid venom allergic individuals. The present invention is thus directed to T cell epitopes of vespid antigen 5 that can anergize T cell responses in sensitive individuals.

11 Claims, 11 Drawing Sheets

FIG. IA

| SEQ ID NO: | | | | |
|---|---|---|---|---|
| 1 | Ves m | NNYCKIKCLKGGVHTACKYG SLKP | NCGNKKVVSYGLTKQEKQDILKE | 1-47 |
| 2 | Ves v | NNYCKIKCLKGGVHTACKYG SLKP | NCGNKvVVSYGLTKQEKQDILKE | 1-47 |
| 3 | Dol a | NNYCKI CpKG tHTLCKYGTSMKP | NCGgKIVKSYGVTNDEKNEIVKR | 1-46 |
| 4 | Dol mA | NNYCKIKCsrG IHTLCKFGTSMKP | NCGsKIVKvhGVsNDEKNEIVnR | 1-47 |
| 5 | Dol mB | NNYCKIKCrkG IHTLCKFGTSMKP | NCGrnVVKayGITNDEKNEIikR | 1-47 |
| 6 | Pol a | VDYCKIKCPSG IHTVCQYGESTKPSKNCAGKVIKSVGPTEEEKKLIVSE | | 1-49 |
| 7 | Pol e | VDYCKIKCPSG IHTVCQYGESTKPSKNCAGKVIKSVGPTEEEKKLIVSE | | 1-49 |

YCKI C G HT C G S KP NC G EK I

| Ves m | HNDFRQKIARGLETRGNPGPQPPAKNMKNLVWsDELAYiAQVVANQCQY | 48-96 |
|---|---|---|
| Ves v | HNDFRQKIARGLETRGNPGPQPPAKNMKNLVWNDELAYvAQVVANQCQY | 48-96 |
| Dol a | HNeFRQKVAqGLETRGNPGPQPPAKNMNILVWNDELAKIAQTWANQCnF | 47-95 |
| Dol mA | HNqFRQKVAKGLETRGkPGPQPPAKNMNVLVWNDELAKIAQTWANQCsF | 48-96 |
| Dol mB | HNdFRQnVAKGLETRGkPGPQPPAKNMNVLVWNDELAKIAQTWANQCdF | 48-96 |
| Pol a | HNRFRQKVAQGLETRGNPGPQPAASDMNDLVWNDELAHIAQVWASQCQFL | 50-99 |
| Pol e | HNRFRQKVAQGLETRGNPGPQPAASDMNDLVWNDELAHIAQVWASQCQFL | 50-99 |

HN FRQ A GLETRG PGPQP A M LVW DELA AQ WA QC

FIG. 1B

```
Ves m   GHDTCRDVAKYQVGQNVALTGSTAAvYnDPVKLVKMWEDEVKDYNPKKKF          97-146
Ves v   GHDTCRDVAKYQVGQNVALTGSTAAkYdDPVKLVKMWEDEVKDYNPKKKF          97-146
Dol a   GHDQCRNTAKYpVGQNVAIASTTGNSYqTMSyLIKMWEDEVKDYNPhKdI          96-145
Dol mA  GHDQCRNTeKYQVGQNVAIASTTGNSYaTMSKLIeMWEnEVKDFNPKKGt          97-146
Dol mB  nHDdCRNTAKYQVGQNIAIsSTTatqfdrpSKLIKqWEdEVteFNYKvGI          97-146
Pol a   VHDKCRNTAKYPVGQNIA YAGGSnLPDVVSLIKLWENEVKDFNYNTGI           100-147
Pol e   VHDKCRNTAKYPVGQNIA YAGGSkLPDVVSLIKLWENEVKDFNYNTGI           100-147

HD  CR   KY  VGQN A    .......  L          WE   EV   N ......
         ─────────────────────────────────────────────────────────────

Ves m   SeNn FLKiGHYTQMVWANTKEVGCGSIKYIQEnWHKHYLVCNYGPSGNFqNEELYQTK  147-204
Ves v   SgNd FLKtGHYTQMVWANTKEVGCGSIKYIQEkWHKHYLVCNYGPSGNFMNEELYQTK  147-204
Dol a   mhNN FSKVGHYTQMVVWGKTKEIGCGSVKYVHTHYLVCNYGPAGNYMNQPvYERK     146-203
Dol mA  igdn nFSKVGHYTQMVVWGKTKEIGCGSVKYIENNWHTHYLVCNYGPAGNYMdQPIYERK 147-205
Dol mB  qnsN FrKVGHYTQMVVWGKTKEIGCGSIKYIEdNWyTHYLVCNYGPgGNdfnQPIYERK  147-204
Pol a   TKQN FAKiGHYTQMVVWGKTKEIGCGSLKYmENNMQNHYLICNYGPAGNYLGQLPYTKK 148-205
Pol e   TKQN FAKIGHYTQMVVWGKTKEIGCGSLKYiENKMQNHYLICNYGPAGNYLGQLPYTKK 148-205

... F K GHYTQMVW    TKE GCGS KY         HYL CNYGP  GN    Y K
          ─────────────────────────────────────────────────────────────
```

FIG. 2

| SEQ ID NO: | | | |
|---|---|---|---|
| 8 | 1 | NNYCKIKCRKGIHTLCKFGT | (1-20) |
| 9 | 2 | GIHTLCKFGTSMKPNCGRNV | (11-30) |
| 10 | 3 | SMKPNCGRNVVKAYGLTNDE | (21-40) |
| 11 | 4 | VKAYGLTNDEKNEILKRHND | (31-50) |
| 12 | 5 | KNEILKRHNDFRQNVAKGLE | (41-60) |
| 13 | 6 | FRQNVAKGLETRGKPGPQPP | (51-70) |
| 14 | 7 | TRGKPGPQPPAKNMNVLVWN | (61-80) |
| 15 | 8 | AKNMNVLVWNDELAKIAQTW | (71-90) |
| 16 | 9 | DELAKIAQTWANQCDFNHDD | (81-100) |
| 17 | 10 | ANQCDFNHDDCRNTAKYQVG | (91-110) |
| 18 | 11 | CRNTAKYQVGQNIAISSTTA | (101-120) |
| 19 | 12 | QNIAISSTTATQFDRPSKLI | (111-130) |
| 20 | 13 | TQFDRPSKLIKQWEDEVTEF | (121-140) |
| 21 | 14 | KQWEDEVTEFNYKVGLQNSN | (131-150) |
| 22 | 15 | NYKVGLQNSNFRKVGHYTQM | (141-160) |
| 23 | 20 | FRKVGHYTQMVWGKT | (151-165) |
| 24 | 16 | HYTQMVWGKTKEIGCGSIKY | (156-175) |
| 25 | 17 | KEIGCGSIKYIEDNWYTHYL | (166-185) |
| 26 | 18 | IEDNWYTHYLVCNYGPGGND | (176-195) |
| 27 | 19 | VCNYGPGGNDFNQPIYERK | (186-204) |

FIG. 3

| SEQ ID NO: | | | | | |
|---|---|---|---|---|---|
| 27 hum | QVQREIVNKHNELRKAV | | SPpaSnmLKMEWSr | | 14-44 |
| 28 mou | QVQREIVNKHNELRRSV | | NPtgSdiILKMEWSi | | 14-44 |
| 29 Ag5 | DEKNEILKRHNDFRQNVAKGLETRGKPGPQPPAKNMNVLVWND | | | | 39-81 |
| hum | EVTTNAQRWANKCTLQHSDPEDRKTSTRCGENL YMSS | | DPTSWSSAI | | 45-89 |
| mou | QATTNAQkWANKCILEHSSKDDRKINIRCGENL YMST | | DPTLWSTVI | | 45-89 |
| Ag5 | ELAKIAQTWANQCDFNHDDCRN TAKYQVGQNIAISSTTATQFDRPSKLI | | | | 82-130 |
| hum | QSWYDEILDFVYGVGPKSPN AVVGHYTQLVWYSTYQVGCGIAYCPNQDS | | | | 90-139 |
| mou | QSWYNENEDFVYGVGAK PN SAVGHYTQLVWYSSFKIGCGIAYCPNQDN | | | | 90-138 |
| Ag5 | KQWEDEVTEFNYKVGLQNSNFRKVGHYTQMVWGKTKEIGCGSIKYIEDNW | | | | 131-180 |
| hum | LKYYYVCQYCPAGNMNRKNTPYQQ | | | | 140-164 |
| mou | LKYFYVCHYCPMGNNVMKKSTPYQQ | | | | 139-163 |
| Ag5 | YTHYLVCNYGPGGNDFNQPIYERK | | | | 181-204 |

SEQUENCE LISTING (1) GENERAL INFORMATION:

(iii) NUMBER OF SEQUENCES: 81

(2) INFORMATION FOR SEQ ID NO:1:

(i) SEQUENCE CHARACTERISTICS:
      (A) LENGTH: 204 amino acids
      (B) TYPE: amino acid
      (C) STRANDEDNESS: single
      (D) TOPOLOGY: linear (ii) MOLECULE TYPE: protein (iii) HYPOTHETICAL: NO (iv) ANTI-SENSE: NO (v) FRAGMENT TYPE:

(vi) ORIGINAL SOURCE:
      (A) ORGANISM: Vespula maculifrons (xi) SEQUENCE DESCRIPTION: SEQ ID NO:1:

```
Asn Asn Tyr Cys Lys Ile Lys Cys Leu Lys Gly Gly Val His Thr Ala
1               5                   10                  15

Cys Lys Tyr Gly Ser Leu Lys Pro Asn Cys Gly Asn Lys Lys Val Val
                20                  25                  30

Ser Tyr Gly Leu Thr Lys Gln Glu Lys Gln Asp Ile Leu Lys Glu His
            35                  40                  45

Asn Asp Phe Arg Gln Lys Ile Ala Arg Gly Leu Glu Thr Arg Gly Asn
    50                  55                  60

Pro Gly Pro Gln Pro Pro Ala Lys Asn Met Lys Asn Leu Val Trp Ser
65                  70                  75                  80

Asp Glu Leu Ala Tyr Ile Ala Gln Val Trp Ala Asn Gln Cys Gln Tyr
                85                  90                  95

Gly His Asp Thr Cys Arg Asp Val Ala Lys Tyr Gln Val Gly Gln Asn
            100                 105                 110

Val Ala Leu Thr Gly Ser Thr Ala Val Tyr Asn Asp Pro Val Lys
            115                 120                 125

Leu Val Lys Met Trp Glu Asp Glu Val Lys Asp Tyr Asn Pro Lys Lys
    130                 135                 140

Lys Phe Ser Glu Asn Asn Phe Leu Lys Ile Gly His Tyr Thr Gln Met
145                 150                 155                 160

Val Trp Ala Asn Thr Lys Glu Val Gly Cys Gly Ser Ile Lys Tyr Ile
                165                 170                 175

Gln Glu Asn Trp His Lys His Tyr Leu Val Cys Asn Tyr Gly Pro Ser
            180                 185                 190

Gly Asn Phe Gln Asn Glu Glu Leu Tyr Gln Thr Lys
            195                 200

(2) INFORMATION FOR SEQ ID NO:2:

(i) SEQUENCE CHARACTERISTICS:
        (A) LENGTH: 204 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE:

(vi) ORIGINAL SOURCE:
        (A) ORGANISM: Vespula vulgaris (xi) SEQUENCE DESCRIPTION: SEQ ID NO:2:

Asn Asn Tyr Cys Lys Ile Lys Cys Leu Lys Gly Gly Val His Thr Ala
1               5                   10                  15

Cys Lys Tyr Gly Ser Leu Lys Pro Asn Cys Gly Asn Lys Val Val Val
                20                  25                  30

Ser Tyr Gly Leu Thr Lys Gln Glu Lys Gln Asp Ile Leu Lys Glu His
            35                  40                  45

Asn Asp Phe Arg Gln Lys Ile Ala Arg Gly Leu Glu Thr Arg Gly Asn
    50                  55                  60

Pro Gly Pro Gln Pro Pro Ala Lys Asn Met Lys Asn Leu Val Trp Asn
65                  70                  75                  80

Asp Glu Leu Ala Tyr Val Ala Gln Val Trp Ala Asn Gln Cys Gln Tyr
                85                  90                  95
```

```
Gly His Asp Thr Cys Arg Asp Val Ala Lys Tyr Gln Val Gly Gln Asn
            100                 105                 110

Val Ala Leu Thr Gly Ser Thr Ala Ala Lys Tyr Asp Asp Pro Val Lys
        115                 120                 125

Leu Val Lys Met Trp Glu Asp Val Lys Asp Tyr Asn Pro Lys Lys
    130                 135                 140

Lys Phe Ser Gly Asn Asp Phe Leu Lys Thr Gly His Tyr Thr Gln Met
145                 150                 155                 160

Val Trp Ala Asn Thr Lys Glu Val Gly Cys Gly Ser Ile Lys Tyr Ile
                165                 170                 175

Gln Glu Lys Trp His Lys His Tyr Leu Val Cys Asn Tyr Gly Pro Ser
            180                 185                 190

Gly Asn Phe Met Asn Glu Glu Leu Tyr Gln Thr Lys
        195                 200
```

(2) INFORMATION FOR SEQ ID NO:3:

(i) SEQUENCE CHARACTERISTICS:
        (A) LENGTH: 203 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE:

(vi) ORIGINAL SOURCE:
        (A) ORGANISM: Dolichovespula arenaria (xi) SEQUENCE DESCRIPTION: SEQ ID NO:3:

```
Asn Asn Tyr Cys Lys Ile Cys Pro Lys Gly Thr His Thr Leu Cys Lys
1               5                   10                  15

Tyr Gly Thr Ser Met Lys Pro Asn Cys Gly Gly Lys Ile Val Lys Ser
            20                  25                  30

Tyr Gly Val Thr Asn Asp Glu Lys Asn Glu Ile Val Lys Arg His Asn
            35                  40                  45

Glu Phe Arg Gln Lys Val Ala Gln Gly Leu Glu Thr Arg Gly Asn Pro
50                  55                  60

Gly Pro Gln Pro Pro Ala Lys Asn Met Asn Leu Leu Val Trp Asn Asp
65                  70                  75                  80

Glu Leu Ala Lys Ile Ala Gln Thr Trp Ala Asn Gln Cys Asn Phe Gly
                85                  90                  95

His Asp Gln Cys Arg Asn Thr Ala Lys Tyr Pro Val Gly Gln Asn Val
            100                 105                 110

Ala Ile Ala Ser Thr Thr Gly Asn Ser Tyr Gln Thr Met Ser Tyr Leu
        115                 120                 125

Ile Lys Met Trp Glu Asp Glu Val Lys Asp Tyr Asn Pro His Lys Asp
    130                 135                 140

Leu Met His Asn Asn Phe Ser Lys Val Gly His Tyr Thr Gln Met Val
145                 150                 155                 160

Trp Gly Lys Thr Lys Glu Ile Gly Cys Gly Ser Val Lys Tyr Ile Glu
                165                 170                 175

Asn Lys Trp His Thr His Tyr Leu Val Cys Asn Tyr Gly Pro Ala Gly
            180                 185                 190
```

Asn Tyr Met Asn Gln Pro Val Tyr Glu Arg Lys
            195                 200

(2) INFORMATION FOR SEQ ID NO:4:

(i) SEQUENCE CHARACTERISTICS:
        (A) LENGTH: 205 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE:

(vi) ORIGINAL SOURCE:
        (A) ORGANISM: Dolichovespula maculata (xi) SEQUENCE DESCRIPTION: SEQ ID NO:4:

Asn Asn Tyr Cys Lys Ile Lys Cys Ser Arg Gly Ile His Thr Leu Cys
1               5                   10                  15

Lys Phe Gly Thr Ser Met Lys Pro Asn Cys Gly Ser Lys Ile Val Lys
            20                  25                  30

Val His Gly Val Ser Asn Asp Glu Lys Asn Glu Ile Val Asn Arg His
        35                  40                  45

Asn Gln Phe Arg Gln Lys Val Ala Lys Gly Leu Glu Thr Arg Gly Asn
    50                  55                  60

Pro Gly Pro Gln Pro Pro Ala Lys Asn Met Asn Val Leu Val Trp Asn
65                  70                  75                  80

Asp Glu Leu Ala Lys Ile Ala Gln Thr Trp Ala Asn Gln Cys Ser Phe
                85                  90                  95

Gly His Asp Gln Cys Arg Asn Thr Glu Lys Tyr Gln Val Gly Gln Asn
            100                 105                 110

Val Ala Ile Ala Ser Thr Thr Gly Asn Ser Tyr Ala Thr Met Ser Lys
        115                 120                 125

Leu Ile Glu Met Trp Glu Asn Glu Val Lys Asp Phe Asn Pro Lys Lys
    130                 135                 140

Gly Thr Ile Gly Asp Asn Asn Phe Ser Lys Val Gly His Tyr Thr Gln
145                 150                 155                 160

Met Val Trp Gly Lys Thr Lys Glu Ile Gly Cys Gly Ser Val Lys Tyr
                165                 170                 175

Ile Glu Asn Asn Trp His Thr His Tyr Leu Val Cys Asn Tyr Gly Pro
            180                 185                 190

Ala Gly Asn Tyr Met Asp Gln Pro Ile Tyr Glu Arg Lys
            195                 200                 205

(2) INFORMATION FOR SEQ ID NO:5:

(i) SEQUENCE CHARACTERISTICS:
        (A) LENGTH: 204 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE:

(vi) ORIGINAL SOURCE:
            (A) ORGANISM: Dolichovespula maculata (xi) SEQUENCE DESCRIPTION: SEQ ID NO:5:

Asn Asn Tyr Cys Lys Ile Lys Cys Arg Lys Gly Ile His Thr Leu Cys
1               5                   10                  15

Lys Phe Gly Thr Ser Met Lys Pro Asn Cys Gly Arg Asn Val Val Lys
            20                  25                  30

Ala Tyr Gly Leu Thr Asn Asp Glu Lys Asn Glu Ile Leu Lys Arg His
            35                  40                  45

Asn Asp Phe Arg Gln Asn Val Ala Lys Gly Leu Glu Thr Arg Gly Lys
50                  55                  60

Pro Gly Pro Gln Pro Pro Ala Lys Asn Met Asn Val Leu Val Trp Asn
65                  70                  75                  80

Asp Glu Leu Ala Lys Ile Ala Gln Thr Trp Ala Asn Gln Cys Asp Phe
                85                  90                  95

Asn His Asp Asp Cys Arg Asn Thr Ala Lys Tyr Gln Val Gly Gln Asn
            100                 105                 110

Ile Ala Ile Ser Ser Thr Thr Ala Thr Gln Phe Asp Arg Pro Ser Lys
            115                 120                 125

Leu Ile Lys Gln Trp Glu Asp Glu Val Thr Glu Phe Asn Tyr Lys Val
130                 135                 140

Gly Leu Gln Asn Ser Asn Phe Arg Lys Val Gly His Tyr Thr Gln Met
145                 150                 155                 160

Val Trp Gly Lys Thr Lys Glu Ile Gly Cys Gly Ser Ile Lys Tyr Ile
                165                 170                 175

Glu Asp Asn Trp Tyr Thr His Tyr Leu Val Cys Asn Tyr Gly Pro Gly
            180                 185                 190

Gly Asn Asp Phe Asn Gln Pro Ile Tyr Glu Arg Lys
            195                 200

(2) INFORMATION FOR SEQ ID NO:6:

(i) SEQUENCE CHARACTERISTICS:
            (A) LENGTH: 205 amino acids
            (B) TYPE: amino acid
            (C) STRANDEDNESS: single
            (D) TOPOLOGY: linear (ii) MOLECULE TYPE: protein (iii) HYPOTHETICAL: NO (iv) ANTI-SENSE: NO (v) FRAGMENT TYPE:

(vi) ORIGINAL SOURCE:
            (A) ORGANISM: Polistes annularis (xi) SEQUENCE DESCRIPTION: SEQ ID NO:6:

Val Asp Tyr Cys Lys Ile Lys Cys Pro Ser Gly Ile His Thr Val Cys
1               5                   10                  15

Gln Tyr Gly Glu Ser Thr Lys Pro Ser Lys Asn Cys Ala Gly Lys Val
            20                  25                  30

Ile Lys Ser Val Gly Pro Thr Glu Glu Lys Lys Leu Ile Val Ser
            35                  40                  45

Glu His Asn Arg Phe Arg Gln Lys Val Ala Gln Gly Leu Glu Thr Arg

-continued

```
            50                  55                  60
Gly Asn Pro Gly Pro Gln Pro Ala Ala Ser Asp Met Asn Asp Leu Val
 65                  70                  75                  80

Trp Asn Asp Glu Leu Ala His Ile Ala Gln Val Trp Ala Ser Gln Cys
                 85                  90                  95

Gln Phe Leu Val His Asp Lys Cys Arg Asn Thr Ala Lys Tyr Pro Val
                100                 105                 110

Gly Gln Asn Ile Ala Tyr Ala Gly Gly Ser Asn Leu Pro Asp Val Val
                115                 120                 125

Ser Leu Ile Lys Leu Trp Glu Asn Glu Val Lys Asp Phe Asn Tyr Asn
130                 135                 140

Thr Gly Ile Thr Lys Gln Asn Phe Ala Lys Ile Gly His Tyr Thr Gln
145                 150                 155                 160

Met Val Trp Gly Lys Thr Lys Glu Ile Gly Cys Gly Ser Leu Lys Tyr
                165                 170                 175

Met Glu Asn Asn Met Gln Asn His Tyr Leu Ile Cys Asn Tyr Gly Pro
                180                 185                 190

Ala Gly Asn Tyr Leu Gly Gln Leu Pro Tyr Thr Lys Lys
                195                 200                 205
```

(2) INFORMATION FOR SEQ ID NO:7:

(i) SEQUENCE CHARACTERISTICS:
        (A) LENGTH: 205 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE:

(vi) ORIGINAL SOURCE:
        (A) ORGANISM: Polistes exclamans (xi) SEQUENCE DESCRIPTION: SEQ ID NO:7:

```
Val Asp Tyr Cys Lys Ile Lys Cys Pro Ser Gly Ile His Thr Val Cys
 1                   5                  10                  15

Gln Tyr Gly Glu Ser Thr Lys Pro Ser Lys Asn Cys Ala Gly Lys Val
                 20                  25                  30

Ile Lys Ser Val Gly Pro Thr Glu Glu Lys Lys Leu Ile Val Ser
                 35                  40                  45

Glu His Asn Arg Phe Arg Gln Lys Val Ala Gln Gly Leu Glu Thr Arg
 50                  55                  60

Gly Asn Pro Gly Pro Gln Pro Ala Ala Ser Asp Met Asn Asp Leu Val
 65                  70                  75                  80

Trp Asn Asp Glu Leu Ala His Ile Ala Gln Val Trp Ala Ser Gln Cys
                 85                  90                  95

Gln Phe Leu Val His Asp Lys Cys Arg Asn Thr Ala Lys Tyr Pro Val
                100                 105                 110

Gly Gln Asn Ile Ala Tyr Ala Gly Gly Ser Lys Leu Pro Asp Val Val
                115                 120                 125

Ser Leu Ile Lys Leu Trp Glu Asn Glu Val Lys Asp Phe Asn Tyr Asn
130                 135                 140

Thr Gly Ile Thr Lys Gln Asn Phe Ala Lys Ile Gly His Tyr Thr Gln
```

```
            145                 150                 155                 160
Met Val Trp Gly Lys Thr Lys Glu Ile Gly Cys Gly Ser Leu Lys Tyr
                    165                 170                 175

Ile Glu Asn Lys Met Gln Asn His Tyr Leu Ile Cys Asn Tyr Gly Pro
            180                 185                 190

Ala Gly Asn Tyr Leu Gly Gln Leu Pro Tyr Thr Lys Lys
            195                 200                 205
```

(2) INFORMATION FOR SEQ ID NO:8:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE:  N-terminal (xi) SEQUENCE DESCRIPTION: SEQ ID NO:8:

```
Asn Asn Tyr Cys Lys Ile Lys Cys Arg Lys Gly Ile His Thr Leu Cys
1               5                   10                  15

Lys Phe Gly Thr
            20
```

(2) INFORMATION FOR SEQ ID NO:9:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:9:

```
Gly Ile His Thr Leu Cys Lys Phe Gly Thr Ser Met Lys Pro Asn Cys
1               5                   10                  15

Gly Arg Asn Val
            20
```

(2) INFORMATION FOR SEQ ID NO:10:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:10:

Ser Met Lys Pro Asn Cys Gly Arg Asn Val Val Lys Ala Tyr Gly Leu
1               5                   10                  15

Thr Asn Asp Glu
            20

(2) INFORMATION FOR SEQ ID NO:11:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:11:

Val Lys Ala Tyr Gly Leu Thr Asn Asp Glu Lys Asn Glu Ile Leu Lys
1               5                   10                  15

Arg His Asn Asp
            20

(2) INFORMATION FOR SEQ ID NO:12:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:12:

Lys Asn Glu Ile Leu Lys Arg His Asn Asp Phe Arg Gln Asn Val Ala
1               5                   10                  15

Lys Gly Leu Glu
            20

(2) INFORMATION FOR SEQ ID NO:13:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:13:

Phe Arg Gln Asn Val Ala Lys Gly Leu Glu Thr Arg Gly Lys Pro Gly
1               5                   10                  15

```
Pro Gln Pro Pro
         20

(2) INFORMATION FOR SEQ ID NO:14:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:14:

Thr Arg Gly Lys Pro Gly Pro Gln Pro Pro Ala Lys Asn Met Asn Val
1               5                  10                  15

Leu Val Trp Asn
         20

(2) INFORMATION FOR SEQ ID NO:15:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:15:

Ala Lys Asn Met Asn Val Leu Val Trp Asn Asp Glu Leu Ala Lys Ile
1               5                  10                  15

Ala Gln Thr Trp
         20

(2) INFORMATION FOR SEQ ID NO:16:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:16:

Asp Glu Leu Ala Lys Ile Ala Gln Thr Trp Ala Asn Gln Cys Asp Phe
1               5                  10                  15

Asn His Asp Asp
         20
```

```
(2) INFORMATION FOR SEQ ID NO:17:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:17:

Ala Asn Gln Cys Asp Phe Asn His Asp Asp Cys Arg Asn Thr Ala Lys
1               5                   10                  15

Tyr Gln Val Gly
            20

(2) INFORMATION FOR SEQ ID NO:18:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:18:

Cys Arg Asn Thr Ala Lys Tyr Gln Val Gly Gln Asn Ile Ala Ile Ser
1               5                   10                  15

Ser Thr Thr Ala
            20

(2) INFORMATION FOR SEQ ID NO:19:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:19:

Gln Asn Ile Ala Ile Ser Ser Thr Thr Ala Thr Gln Phe Asp Arg Pro
1               5                   10                  15

Ser Lys Leu Ile
            20

(2) INFORMATION FOR SEQ ID NO:20:

(i) SEQUENCE CHARACTERISTICS:
        (A) LENGTH: 20 amino acids
```

(B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:20:

Thr Gln Phe Asp Arg Pro Ser Lys Leu Ile Lys Gln Trp Glu Asp Glu
1               5                   10                  15

Val Thr Glu Phe
            20

(2) INFORMATION FOR SEQ ID NO:21:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:21:

Lys Gln Trp Glu Asp Glu Val Thr Glu Phe Asn Tyr Lys Val Gly Leu
1               5                   10                  15

Gln Asn Ser Asn
            20

(2) INFORMATION FOR SEQ ID NO:22:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:22:

Asn Tyr Lys Val Gly Leu Gln Asn Ser Asn Phe Arg Lys Val Gly His
1               5                   10                  15

Tyr Thr Gln Met
            20

(2) INFORMATION FOR SEQ ID NO:23:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:23:

Phe Arg Lys Val Gly His Tyr Thr Gln Met Val Trp Gly Lys Thr
1               5                   10                  15

NFORMATION FOR SEQ ID NO:24:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:24:

His Tyr Thr Gln Met Val Trp Gly Lys Thr Lys Glu Ile Gly Cys Gly
1               5                   10                  15

Ser Ile Lys Tyr
            20

(2) INFORMATION FOR SEQ ID NO:25:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:25:

Lys Glu Ile Gly Cys Gly Ser Ile Lys Tyr Ile Glu Asp Asn Trp Tyr
1               5                   10                  15

Thr His Tyr Leu
            20

(2) INFORMATION FOR SEQ ID NO:26:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:26:

Ile Glu Asp Asn Trp Tyr Thr His Tyr Leu Val Cys Asn Tyr Gly Pro
1               5                   10                  15

Gly Gly Asn Asp
            20

(2) INFORMATION FOR SEQ ID NO:27:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO:27:

Val Cys Asn Tyr Gly Pro Gly Gly Asn Asp Phe Asn Gln Pro Ile Tyr
1               5                   10                  15

Glu Arg Lys (2) INFORMATION FOR SEQ ID NO:28:

(i) SEQUENCE CHARACTERISTICS:
        (A) LENGTH: 151 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
        (A) ORGANISM: Homo sapiens (xi) SEQUENCE DESCRIPTION: SEQ ID NO:28:

Gln Val Gln Arg Glu Ile Val Asn Lys His Asn Glu Leu Arg Lys Ala
1               5                   10                  15

Val Ser Pro Pro Ala Ser Asn Met Leu Lys Met Glu Trp Ser Arg Glu
            20                  25                  30

Val Thr Thr Asn Ala Gln Arg Trp Ala Asn Lys Cys Thr Leu Gln His
                35                  40                  45

Ser Asp Pro Glu Asp Arg Lys Thr Ser Thr Arg Cys Gly Glu Asn Leu
        50                  55                  60

Tyr Met Ser Ser Asp Pro Thr Ser Trp Ser Ser Ala Ile Gln Ser Trp
65                  70                  75                  80

Tyr Asp Glu Ile Leu Asp Phe Val Tyr Gly Val Gly Pro Lys Ser Pro
                85                  90                  95

Asn Ala Val Val Gly His Tyr Thr Gln Leu Val Trp Tyr Ser Thr Tyr
                100                 105                 110

Gln Val Gly Cys Gly Ile Ala Tyr Cys Pro Asn Gln Asp Ser Leu Lys
                115                 120                 125

```
Tyr Tyr Tyr Val Cys Gln Tyr Cys Pro Ala Gly Asn Asn Met Asn Arg
    130                 135                 140
Lys Asn Thr Pro Tyr Gln Gln
145                 150
```

(2) INFORMATION FOR SEQ ID NO:29:

(i) SEQUENCE CHARACTERISTICS:
        (A) LENGTH: 150 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
        (A) ORGANISM: Mus musculus (xi) SEQUENCE DESCRIPTION: SEQ ID NO:29:

```
Gln Val Gln Arg Glu Ile Val Asn Lys His Asn Glu Leu Arg Arg Ser
1               5                   10                  15
Val Asn Pro Thr Gly Ser Asp Ile Leu Lys Met Glu Trp Ser Ile Gln
                20                  25                  30
Ala Thr Thr Asn Ala Gln Lys Trp Ala Asn Lys Cys Ile Leu Glu His
            35                  40                  45
Ser Ser Lys Asp Asp Arg Lys Ile Asn Ile Arg Cys Gly Glu Asn Leu
50                  55                  60
Tyr Met Ser Thr Asp Pro Thr Leu Trp Ser Thr Val Ile Gln Ser Trp
65                  70                  75                  80
Tyr Asn Glu Asn Glu Asp Phe Val Tyr Gly Val Gly Ala Lys Pro Asn
                85                  90                  95
Ser Ala Val Gly His Tyr Thr Gln Leu Val Trp Tyr Ser Ser Phe Lys
            100                 105                 110
Ile Gly Cys Gly Ile Ala Tyr Cys Pro Asn Gln Asp Asn Leu Lys Tyr
        115                 120                 125
Phe Tyr Val Cys His Tyr Cys Pro Met Gly Asn Asn Val Met Lys Lys
    130                 135                 140
Ser Thr Pro Tyr Gln Gln
145                 150
```

(2) INFORMATION FOR SEQ ID NO:30:

(i) SEQUENCE CHARACTERISTICS:
        (A) LENGTH: 166 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
        (A) ORGANISM: Vespid (xi) SEQUENCE DESCRIPTION: SEQ ID NO:30:

```
Asp Glu Lys Asn Glu Ile Leu Lys Arg His Asn Asp Phe Arg Gln Asn
1               5                   10                  15

Val Ala Lys Gly Leu Glu Thr Arg Gly Lys Pro Gly Pro Gln Pro Pro
            20                  25                  30

Ala Lys Asn Met Asn Val Leu Val Trp Asn Asp Glu Leu Ala Lys Ile
            35                  40                  45

Ala Gln Thr Trp Ala Asn Gln Cys Asp Phe Asn His Asp Asp Cys Arg
        50                  55                  60

Asn Thr Ala Lys Tyr Gln Val Gly Gln Asn Ile Ala Ile Ser Ser Thr
65                  70                  75                  80

Thr Ala Thr Gln Phe Asp Arg Pro Ser Lys Leu Ile Lys Gln Trp Glu
                85                  90                  95

Asp Glu Val Thr Glu Phe Asn Tyr Lys Val Gly Leu Gln Asn Ser Asn
                100                 105                 110

Phe Arg Lys Val Gly His Tyr Thr Gln Met Val Trp Gly Lys Thr Lys
            115                 120                 125

Glu Ile Gly Cys Gly Ser Ile Lys Tyr Ile Glu Asp Asn Trp Tyr Thr
            130                 135                 140

His Tyr Leu Val Cys Asn Tyr Gly Pro Gly Gly Asn Asp Phe Asn Gln
145                 150                 155                 160

Pro Ile Tyr Glu Arg Lys
                165

(2) INFORMATION FOR SEQ ID NO:31:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:31:

Xaa Asx Tyr Cys Lys Ile Xaa Cys Xaa Xaa Gly Xaa Xaa His Thr Xaa
1               5                   10                  15

Cys Xaa Xaa Gly
            20

(2) INFORMATION FOR SEQ ID NO:32:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:32:

Gly Xaa Xaa His Thr Xaa Cys Xaa Xaa Gly Xaa Ser Xaa Lys Pro Xaa
```

```
                 1               5              10              15
Xaa Asn Cys Xaa Xaa Xaa Xaa Xaa
                20
```

(2) INFORMATION FOR SEQ ID NO:33:

(i) SEQUENCE CHARACTERISTICS:
        (A) LENGTH: 34 amino acids
        (B) TYPE: amino acid
        (C) STRANDEDNESS: single
        (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:33:

```
Xaa Asx Tyr Cys Lys Ile Xaa Cys Xaa Xaa Gly Xaa Xaa His Thr Xaa
1               5                  10                  15
Cys Xaa Xaa Gly Xaa Ser Xaa Lys Pro Xaa Xaa Asn Cys Xaa Xaa Xaa
                20                  25                  30
Xaa Xaa
```

(2) INFORMATION FOR SEQ ID NO:34:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:34:

```
Lys Xaa Xaa Ile Xaa Xaa Xaa His Asn Xaa Phe Arg Gln Lys Xaa Ala
1               5                  10                  15
Xaa Gly Leu Glu
                20
```

(2) INFORMATION FOR SEQ ID NO:35:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:35:

```
Phe Arg Gln Lys Xaa Ala Xaa Gly Leu Glu Thr Arg Gly Xaa Pro Gly
1               5                  10                  15
```

```
Pro Gln Pro Xaa
        20
```

(2) INFORMATION FOR SEQ ID NO:36:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:36:

```
Lys Xaa Xaa Ile Xaa Xaa Xaa His Asn Xaa Phe Arg Gln Lys Xaa Ala
1               5                   10                  15
Xaa Gly Leu Glu Thr Arg Gly Xaa Pro Gly Pro Gln Pro Xaa
            20                  25                  30
```

(2) INFORMATION FOR SEQ ID NO:37:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:37:

```
Asp Glu Leu Ala Xaa Xaa Ala Gln Xaa Trp Ala Xaa Gln Cys Xaa Xaa
1               5                   10                  15
Xaa Xaa His Asp
        20
```

(2) INFORMATION FOR SEQ ID NO:38:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:38:

```
Asn Xaa Xaa Xaa Xaa Xaa Xaa Xaa Xaa Asx Xaa Phe Xaa Lys Xaa Gly
1               5                   10                  15
His Tyr Thr Gln Met
        20
```

```
(2) INFORMATION FOR SEQ ID NO:39:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:39:

Phe Xaa Lys Xaa Gly His Tyr Thr Gln Met Val Trp Xaa Xaa Thr
1               5                  10                  15

NFORMATION FOR SEQ ID NO:40:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:40:

Asn Xaa Xaa Xaa Xaa Xaa Xaa Xaa Xaa Asx Xaa Phe Xaa Lys Xaa Gly
1               5                  10                  15
His Tyr Thr Gln Met Val Trp Xaa Xaa Thr
            20                  25

(2) INFORMATION FOR SEQ ID NO:41:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:41:

Xaa Glx Xaa Xaa Xaa Xaa Xaa His Tyr Leu Xaa Cys Asn Tyr Gly Pro
1               5                  10                  15
Xaa Gly Asn Xaa Xaa Xaa
            20

(2) INFORMATION FOR SEQ ID NO:42:

(i) SEQUENCE CHARACTERISTICS:
        (A) LENGTH: 32 amino acids
        (B) TYPE: amino acid
        (C) STRANDEDNESS: single
        (D) TOPOLOGY: linear
```

(ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:42:

Asn Asn Tyr Cys Lys Ile Lys Cys Arg Lys Gly Ile His Thr Leu Cys
1               5                   10                  15

Lys Phe Gly Thr Gly Thr Ser Met Lys Pro Asn Cys Gly Arg Asn Val
            20                  25                  30

(2) INFORMATION FOR SEQ ID NO:43:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:43:

Lys Asn Glu Ile Leu Lys Arg His Asn Asp Phe Arg Gln Asn Val Ala
1               5                   10                  15

Lys Gly Leu Glu Thr Arg Gly Lys Pro Gly Pro Gln Pro Pro
            20                  25                  30

(2) INFORMATION FOR SEQ ID NO:44:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:44:

Asn Tyr Lys Val Gly Leu Gln Asn Ser Asn Phe Arg Lys Val Gly His
1               5                   10                  15

Tyr Thr Gln Met Val Trp Gly Lys Thr
            20                  25

(2) INFORMATION FOR SEQ ID NO:45:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:45:

Asn Asn Tyr Cys Lys Ile Lys Cys Leu Lys Gly Gly Val His Thr Ala
1               5                  10                 15

Cys Lys Tyr Gly Ser Leu Lys Pro Asn Cys Gly Asn Lys Lys Val
            20                  25                  30

(2) INFORMATION FOR SEQ ID NO:46:

(i) SEQUENCE CHARACTERISTICS:
             (A) LENGTH: 31 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:46:

Asn Asn Tyr Cys Lys Ile Lys Cys Leu Lys Gly Gly Val His Thr Ala
1               5                  10                 15

Cys Lys Tyr Gly Ser Leu Lys Pro Asn Cys Gly Asn Lys Val Val
            20                  25                  30

(2) INFORMATION FOR SEQ ID NO:47:

(i) SEQUENCE CHARACTERISTICS:
             (A) LENGTH: 31 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:47:

Asn Asn Tyr Cys Lys Ile Cys Pro Lys Gly Thr His Thr Leu Cys Lys
1               5                  10                 15

Tyr Gly Thr Ser Met Lys Pro Asn Cys Gly Gly Lys Ile Val Lys
            20                  25                  30

(2) INFORMATION FOR SEQ ID NO:48:

(i) SEQUENCE CHARACTERISTICS:
             (A) LENGTH: 32 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:48:

Asn Asn Tyr Cys Lys Ile Lys Cys Ser Arg Gly Ile His Thr Leu Cys
1               5                   10                  15

Lys Phe Gly Thr Ser Met Lys Pro Asn Cys Gly Ser Lys Ile Val Lys
                20                  25                  30

(2) INFORMATION FOR SEQ ID NO:49:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:49:

Asn Asn Tyr Cys Lys Ile Lys Cys Arg Lys Gly Ile His Thr Leu Cys
1               5                   10                  15

Lys Phe Gly Thr Ser Met Lys Pro Asn Cys Gly Arg Asn Val Val Lys
                20                  25                  30

(2) INFORMATION FOR SEQ ID NO:50:

(i) SEQUENCE CHARACTERISTICS:
        (A) LENGTH: 34 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:50:

Val Asp Tyr Cys Lys Ile Lys Cys Pro Ser Gly Ile His Thr Val Cys
1               5                   10                  15

Gln Tyr Gly Glu Ser Thr Lys Pro Ser Lys Asn Cys Ala Gly Lys Val
                20                  25                  30

Ile Lys (2) INFORMATION FOR SEQ ID NO:51:

(i) SEQUENCE CHARACTERISTICS:
        (A) LENGTH: 34 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:51:

```
Val Asp Tyr Cys Lys Ile Lys Cys Pro Ser Gly Ile His Thr Val Cys
1               5                   10                  15

Gln Tyr Gly Glu Ser Thr Lys Pro Ser Lys Asn Cys Ala Gly Lys Val
                20                  25                  30

Ile Lys
```

(2) INFORMATION FOR SEQ ID NO:52:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:52:

```
Tyr Asn Tyr Cys Asn Leu Gln Ser Cys Lys Arg Asn Asn Ala Ile His
1               5                   10                  15

Thr Met Cys Gln Tyr Thr Ser Pro Thr Pro Gly Pro Met Cys Leu Glu
                20                  25                  30

Tyr Ser Asn
        35
```

(2) INFORMATION FOR SEQ ID NO:53:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:53:

```
Lys Gln Asp Ile Leu Lys Glu His Asn Asp Phe Arg Gln Lys Ile Ala
1               5                   10                  15

Arg Gly Leu Glu Thr Arg Gly Asn Pro Gly Pro Gln Pro Pro Ala
                20                  25                  30
```

(2) INFORMATION FOR SEQ ID NO:54:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:54:

Lys Gln Asp Ile Leu Lys Glu His Asn Asp Phe Arg Gln Lys Ile Ala
1               5                   10                  15

Arg Gly Leu Glu Thr Arg Gly Asn Pro Gly Pro Gln Pro Pro Ala
            20                  25                  30

(2) INFORMATION FOR SEQ ID NO:55:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:55:

Lys Asn Glu Ile Val Lys Arg His Asn Glu Phe Arg Gln Lys Val Ala
1               5                   10                  15

Gln Gly Leu Glu Thr Arg Gly Asn Pro Gly Pro Gln Pro Pro Ala
            20                  25                  30

(2) INFORMATION FOR SEQ ID NO:56:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:56:

Lys Asn Glu Ile Val Asn Arg His Asn Gln Phe Arg Gln Lys Val Ala
1               5                   10                  15

Lys Gly Leu Glu Thr Arg Gly Asn Pro Gly Pro Gln Pro Pro Ala
            20                  25                  30

(2) INFORMATION FOR SEQ ID NO:57:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:57:

Lys Asn Glu Ile Leu Lys Arg His Asn Asp Phe Arg Gln Asn Val Ala
1               5                   10                  15

Lys Gly Leu Glu Thr Arg Gly Lys Pro Gly Pro Gln Pro Pro Ala
            20                  25                  30

(2) INFORMATION FOR SEQ ID NO:58:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:58:

Lys Lys Leu Ile Val Ser Glu His Asn Arg Phe Arg Gln Lys Val Ala
1               5                   10                  15

Gln Gly Leu Glu Thr Arg Gly Asn Pro Gly Pro Gln Pro Ala Ala
            20                  25                  30

(2) INFORMATION FOR SEQ ID NO:59:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:59:

Lys Lys Leu Ile Val Ser Glu His Asn Arg Phe Arg Gln Lys Val Ala
1               5                   10                  15

Gln Gly Leu Glu Thr Arg Gly Asn Pro Gly Pro Gln Pro Ala Ala
            20                  25                  30

(2) INFORMATION FOR SEQ ID NO:60:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:60:

Lys Asp Ala Ile Val Asn Lys His Asn Glu Leu Arg Gln Arg Val Ala
1               5                   10                  15

Ser Gly Lys Glu Met Arg Gly Thr Asn Gly Pro Gln Pro Pro Ala
            20                  25                  30

```
(2) INFORMATION FOR SEQ ID NO:61:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:61:

Asp Glu Leu Ala Tyr Ile Ala Gln Val Trp Ala Asn Gln Cys Gln Tyr
1               5                  10                  15

Gly His Asp Thr
            20

(2) INFORMATION FOR SEQ ID NO:62:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:62:

Asp Glu Leu Ala Tyr Val Ala Gln Val Trp Ala Asn Gln Cys Gln Tyr
1               5                  10                  15

Gly His Asp Thr
            20

(2) INFORMATION FOR SEQ ID NO:63:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:63:

Asp Glu Leu Ala Lys Ile Ala Gln Thr Trp Ala Asn Gln Cys Asn Phe
1               5                  10                  15

Gly His Asp Gln
            20

(2) INFORMATION FOR SEQ ID NO:64:

(i) SEQUENCE CHARACTERISTICS:
```

```
            (A) LENGTH: 20 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:64:

Asp Glu Leu Ala Lys Ile Ala Gln Thr Trp Ala Asn Gln Cys Ser Phe
1               5                  10                  15

Gly His Asp Gln
            20

(2) INFORMATION FOR SEQ ID NO:65:

(i) SEQUENCE CHARACTERISTICS:
            (A) LENGTH: 21 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:65:

Asp Glu Leu Ala His Ile Ala Gln Val Trp Ala Ser Gln Cys Gln Phe
1               5                  10                  15

Leu Val His Asp Lys
            20

(2) INFORMATION FOR SEQ ID NO:66:

(i) SEQUENCE CHARACTERISTICS:
            (A) LENGTH: 21 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:66:

Asp Glu Leu Ala His Ile Ala Gln Val Trp Ala Ser Gln Cys Gln Phe
1               5                  10                  15

Leu Val His Asp Lys
            20

(2) INFORMATION FOR SEQ ID NO:67:

(i) SEQUENCE CHARACTERISTICS:
            (A) LENGTH: 20 amino acids
            (B) TYPE: amino acid
            (C) STRANDEDNESS: single
            (D) TOPOLOGY: linear
```

(ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:67:

Pro Glu Leu Ala Thr Ile Ala Gln Arg Trp Ala Asn Gln Cys Thr Glu
1               5                  10                  15

Glu His Asp Ala
            20

(2) INFORMATION FOR SEQ ID NO:68:

(i) SEQUENCE CHARACTERISTICS:
             (A) LENGTH: 25 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:68:

Asn Pro Lys Lys Lys Phe Ser Glu Asn Asn Phe Leu Lys Ile Gly His
1               5                  10                  15

Tyr Thr Gln Met Val Trp Ala Asn Thr
            20                  25

(2) INFORMATION FOR SEQ ID NO:69:

(i) SEQUENCE CHARACTERISTICS:
             (A) LENGTH: 25 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:69:

Asn Pro Lys Lys Lys Phe Ser Gly Asn Asp Phe Leu Lys Thr Gly His
1               5                  10                  15

Tyr Thr Gln Met Val Trp Ala Asn Thr
            20                  25

(2) INFORMATION FOR SEQ ID NO:70:

(i) SEQUENCE CHARACTERISTICS:
             (A) LENGTH: 25 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:70:

Asn Pro His Lys Asp Leu Met His Asn Asn Phe Ser Lys Val Gly His
1               5                  10                  15

Tyr Thr Gln Met Val Trp Gly Lys Thr
                20                  25

(2) INFORMATION FOR SEQ ID NO:71:

(i) SEQUENCE CHARACTERISTICS:
            (A) LENGTH: 26 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:71:

Asn Pro Lys Lys Gly Thr Ile Gly Asp Asn Phe Ser Lys Val Gly
1               5                  10                  15

His Tyr Thr Gln Met Val Trp Gly Lys Thr
                20                  25

(2) INFORMATION FOR SEQ ID NO:72:

(i) SEQUENCE CHARACTERISTICS:
            (A) LENGTH: 25 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:72:

Asn Tyr Asn Thr Gly Ile Thr Lys Gln Asn Phe Ala Lys Ile Gly His
1               5                  10                  15

Tyr Thr Gln Met Val Trp Gly Lys Thr
                20                  25

(2) INFORMATION FOR SEQ ID NO:73:

(i) SEQUENCE CHARACTERISTICS:
            (A) LENGTH: 25 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:73:

Asn Tyr Asn Thr Gly Ile Thr Lys Gln Asn Phe Ala Lys Ile Gly His
1               5                   10                  15

Tyr Thr Gln Met Val Trp Gly Lys Thr
            20                  25

(2) INFORMATION FOR SEQ ID NO:74:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:74:

Asn Tyr Asn Thr Gly Ile Ser Phe Pro Ser Asp Asp Asn Ile Leu Met
1               5                   10                  15

Lys Val Glu His Tyr Thr Gln Ile Val Trp Ala Lys Thr
            20                  25

(2) INFORMATION FOR SEQ ID NO:75:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:75:

Ile Gln Glu Asn Trp His Lys His Tyr Leu Val Cys Asn Tyr Gly Pro
1               5                   10                  15

Ser Gly Asn Phe
            20

(2) INFORMATION FOR SEQ ID NO:76:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:76:

Ile Gln Glu Lys Trp His Lys His Tyr Leu Val Cys Asn Tyr Gly Pro

```
                1               5              10              15
Ser Gly Asn Phe
            20

(2) INFORMATION FOR SEQ ID NO:77:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:77:

Ile Glu Asn Lys Trp His Thr His Tyr Leu Val Cys Asn Tyr Gly Pro
1               5                  10                  15
Ala Gly Asn Tyr
            20

(2) INFORMATION FOR SEQ ID NO:78:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:78:

Ile Glu Asn Asn Trp His Thr His Tyr Leu Val Cys Asn Tyr Gly Pro
1               5                  10                  15
Ala Gly Asn Tyr
            20

(2) INFORMATION FOR SEQ ID NO:79:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:79:

Met Glu Asn Asn Met Gln Asn His Tyr Leu Ile Cys Asn Tyr Gly Pro
1               5                  10                  15
Ala Gly Asn Tyr
            20
```

(2) INFORMATION FOR SEQ ID NO:80:

(i) SEQUENCE CHARACTERISTICS:
       (A) LENGTH: 20 amino acids
       (B) TYPE: amino acid
       (C) STRANDEDNESS: single
       (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:80:

Ile Glu Asn Lys Met Gln Asn His Tyr Leu Ile Cys Asn Tyr Gly Pro
1               5                  10                  15

Ala Gly Asn Tyr
            20

(2) INFORMATION FOR SEQ ID NO:81:

(i) SEQUENCE CHARACTERISTICS:
       (A) LENGTH: 20 amino acids
       (B) TYPE: amino acid
       (C) STRANDEDNESS: single
       (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:81:

Glu Pro Asp Asn Trp Thr Lys His Tyr Leu Val Cys Asn Tyr Gly Pro
1               5                  10                  15

Ala Gly Asn Val
            20

IMMUNOMODULATORY PEPTIDES OF VESPID ANTIGEN 5

This Application is a Division of application Ser. No. 08/614,935 filed Mar. 11, 1996 now U.S. Pat. No. 5,804,201, issued Sep. 8, 1998.

The research leading to the present invention was supported by United States Public Health Service Grant No. AI-17021. The government may have certain rights in the invention.

FIELD OF THE INVENTION

The present invention is directed to immunogenic peptides from vespid antigen 5. These immunogenic peptides can be used in immunotherapy for vespid venom allergic individuals. The present invention is thus directed to T cell epitopes of vespid antigen 5 that can anergize T cell responses in sensitive individuals.

BACKGROUND OF THE INVENTION

Biochemical Aspects of Insect Venom Allergens

Insect sting allergy to bees and vespids is of common occurrence. The vespids include hornets, yellowjackets and wasps [Golden, et al., *Am. Med. Assoc.*, 262:240 (1989)]. Susceptible people can be sensitized on exposure to minute amounts of venom proteins; as little as 2–10 µg of protein is injected into the skin on a single sting by a vespid [Hoffman and Jacobson, *Ann. Allergy.*, 52:276(1984)].

Indeed, venom allergens from insects of the Hymenoptera order have been extensively studied. These insects are bees, vespids and fire ants. The bees include honey bees (*Apis melifera*) and bumble bees (*Bombus pennsylvanicua*). The vespids include hornets (Dolichovespula spp.; *Vespa crabo*), yellow jackets (Vespula spp.), and paper wasps (Polistes spp.). In Table 1 are listed the venom allergens from these insects with known primary structures.

TABLE 1

Cloned and/or sequenced insect venom allergens

| Allergen name[1] | Common name | Mol. Size[2] | Recombinant protein[3] unfolded | folded |
|---|---|---|---|---|
| Bumble bee, *Bombus pennsylvanicus* | | | | |
| Bom p 1 | phospholipase $A_2$ | 16 kd | – | – |
| Bom p 4 | protease | 28 kd | – | – |
| Honey bee, *Apis melifera* | | | | |
| Api m 1 | phospholipase $A_2$ | 16 kd | + | + |
| Api m 2 | hyaluronidase | 39 kd | + | + |
| Api m 3 | acid phosphatase | 43 kd | – | – |
| Api m 4 | melittin | 3 kd | – | – |
| Fire ant, *Solenopsis invicta* | | | | |
| Sol i 1 | phospholipase $A_1$ | 37 kd | – | – |
| Sol i 2 | | 30 kd | – | – |
| Sol i 3 | antigen 5 | 23 kd | – | + |
| Sol i 4 | | 20 kd | – | – |
| White face hornet, *Dolichovespula maculata* | | | | |
| Dol m 1 | phospholipase $A_1$ | 34 kd | + | – |
| Dol m 2 | hyaluronidase | 38 kd | + | – |
| Dol m 5 | antigen 5 | 23 kd | + | + |
| European hornet, *Vespa crabo* | | | | |
| Vesp c 1 | phospholipase $A_1$ | 23 kd | – | – |
| Vesp c 5 | antigen 5 | 23 kd | – | – |
| Paper wasp, *Polistes annularis* | | | | |
| Pol 1 5[5] | antigen 5 | 23 kd | + | – |
| Yellow jacket, *Vepula vulgaris* | | | | |
| Ves v 1 | phospholipase $A_1$ | 34 kd | + | – |
| Ves v 2 | hyaluronidase | 38 kd | + | – |
| Ves v 5[5] | antigen 5 | 23 kd | + | – |

Footnotes
[1]Allergen names are designated according to an accepted nomenclature system [King et al., WHO Bulletin, 72:797 (1994)].
[2]Several allergens are glycoproteins, and the molecular size given refers only to the protein portion.
[3] + and – signs refer to the availability of recombinant proteins.
[4]Sequence of antigen 5 from *S. richteria* is known [Smith & Hoffman, J. Allerg. Clin. Imunol., 89:293 (1992)].
[5]Sequences of antigen 5s from several other vespids are known; *D. arenaria* [Lu et al., J. Immunol. 150:2823 (1993)], *P. exclamans* and *P. fuscatus*, and *V. flavopilosa, V. germanica, V. maculifrons, V. pennsylvanica, V. spamosa* and *V. vidua* [Hoffman et al., Int. Archs. Allergy App. Immunol., 84:24 (1987)].

There are many species of hornets (genus Dolichovespula), yellowjackets (genus Vespula) and wasp (genus Polistes) in North America [Akre, et al., "Yellowjackets of America North of Mexico," Agriculture Hand book No. 552, US Department of Agriculture (1980)]. The vespids have similar venom compositions [King, et al., *Biochemistry*, 17:5165 (1978); King, et al., *Mol. Immunol.* 20:297 (1983); King, et al., *Arch. Biochem. Biophys.* 230:1 (1984); King, et al., *J. Allergy and Clin. Immunol.*, 75:621 (1985); King, *J. Allergy Clin. Immunol.*, 79:113 (1987); Hoffman, *J. Allergy and Clin. Immunol.*, 75:611 (1985)]. Their venom each contains three major venom allergens, phospholipase (37 kD), hyaluronidase (43 kD) and antigen 5 (23 kD) of as yet unklnown biologic function. Homologous venom allergens from hornets, yellow jackets, and paper wasps have high degrees of sequence identity ranging form about 70% for antigen 5s to about 90% for hyaluronidases [Lu et al., *J. Immunol.*, 150:2823 (1993)].

Antigen 5 from several species each of hornets, yellowjackets and paper wasps have been cloned and/or sequenced [Fang et al., *Proc. Natl. Acad. Sci., USA*, 85:895–899 (1988); Lu et al., supra; Hoffman, *J. Allergy Clin. Immunol.*, 92:707–716 (1993)]. For phospholipases and hyaluronidases only those from hornets and yellowjackets have been cloned and/or sequenced [Soladatova et al., *FEBS Letters*, 320:145–149 (1993); Lu et al., *J. Biol. Chem.*, 270:4457–4465 (1995); King et al., *J. Allergy Clin. Immunol.*, In press (1996); Hoffman, *Int. Arch. Allergy Immunol.*, 104:184–190 (1994)]. One common feature of these venom proteins is their varying extents of sequence homology with mammalian proteins.

White faced hornet (*Dolichovespula maculata*) has three forms of antigen 5. Two of these forms, Dol m 5.01 and 5.02, differ in 23% of their sequences, and they are antigenically cross reactive at both B and T cell levels [Fang et al., *Proc. Natl. Acad. Sci., USA*, 85:895–899 (1988); Lu et al., *J. Immunol.*, 150:2823–2830 (1993)]. The studies described here were made with Dol m 5.02, also referred to as hornet Ag5 form 2. The amino acid sequences of Dol m 5.01 and 5.02, as well as those of the homologous antigen 5s from yellow hornet (*Dolichovespula arenaria*), two species of yellowjacket (*Vespula maculifrons* and *vulgaris*) and two species of papers wasps (*Polistes annularis* and *excoamans*) are given in FIG. 1.

Fire ant venom contains four allergens. They are antigen 5, phospholipase $A_1$, and Sol i 2 and 4. Fire ant antigen 5 has about 50% sequence identity with vespid antigen 5 [Hoffman, *J. Allergy Clin. Immunol.*, 91:71 (1995)]. Only partial sequence data is available for fire ant phospholipase, and it shows sequence identity with vespid phospholipase $A_1$ [Hoffman, *J. Allergy Clin. Immunol.*, 95:372 (1995)].

Bumble bee venom has two allergens of known sequences; phospholipase $A_2$ and protease. But honey bee venom has four allergens of know sequences; acid phosphatase, phospholipase $A_2$, hyaluronidase and a cytolytic peptide melittin. The two bee venom phospholipase $A_2$ have extensive sequence identity and they are not-related to vespid phospholipase $A_1$ [Hoffman, "Hymenoptia Venom Proteins" in *National Toxins*, R. B. Singh (ed.), Plenum Publishing 6 (1996)]. Honey bee venom hyaluronidase has about 55% sequence identity with the homologous vespid hyaluronidases.

In addition to the insect venom allergens described above, the complete amino acid sequence of several major allergens from different grass [Perez, et al., *J. Biol. Chem.*, 265:16210 (1990); Ansari, et al., *Biochemistry*, 26:8665 (1989); Silvanovich, et al., *J. Biol. Chem.*, 266:1204 (1991)], tree pollen [Breiteneder, *EMBO J.*, 8:1935(1989); Valenta, et al., *Science*, 253:557 (1991)], weed pollen [Rafnar, et al., *J. Biol. Chem.*, 266:1229 (1991); Griffith, et al., *Int. Arch. Allergy Appl. Immunol.*, 96:296 (1991)], mites (Chua, et al., *J. Exp. Med.*, 167:175 (1988)], cat dander [Griffith, et al., *Gene.*, 113:263 (1992)], and mold [Aruda, et al., *J. Exp. Med.*, 172:1529 (1990); Han, et al., *J. Allergy Clin. Immunol.*, 87:327 (1991)] have been reported in the past few years. These major allergens are proteins of 10–40 kD and they have widely different biological functions. Nearly all allergens of known sequences have a varying extent of sequence similarity with other proteins in our environment.

T and B Cell Epitopes of Allergens

Antibody responses to proteins require the collaboration of T helper and B lymphocytes and antigen presenting cells (APC). The antigen receptors of B cells are the membrane-bound antibody (Ab) molecules, which recognize and bind immunogens directly. The antigen receptors of T cells (TCR) only recognize and bind complexes of antigenic peptide-MHC class II molecule. Immunogens are first processed by APC into peptides that are presented on the surface of APC in association with the MHC class II molecules [Unanue, *Current Opinion in Immunol*, 4:63 (1992)]. As MHC molecules are highly polymorphic in individuals, they have different specificity of binding antigenic peptides [Rothbard and Gefter, *Ann. Rev. Immunol.*, 9:527 (1991)]. This is one mechanism for genetic control of immune response.

T helper cells are activated when the antigen receptor binds the peptide-MHC complex on the surface of APC. Activated T cells secrete lymphokines. In mice [Street and Mosmann, *FASEB J.*, 5:171 (1991)] and apparently in humans [Wierenga. et at., *J. Immunol.*, 144:4651 (1990); Parronchi, et al., *Proc. Natl. Acad. Sci. USA.*, 88:4538 (1991)] the T helper cells can be divided into different types on the basis of their patterns of lymphokine production. Primarily, T helper cells divide into two groups: TH1 cells producing IL-2 and IFN-γ, and TH2 cells producing IL-4 and IL-5. These lymphokines in turn influence the antigen-activated B cells to differentiate and proliferate into plasma cells secreting Abs of different isotypes. IL-4 is one lymphokine known to influence IgE synthesis [Finkelman. et al., *Ann. Rev. Immunol.*, 8:303 (1990)].

It is believed that the entire accessible surface of a protein molecule can be recognized as epitopes by the antigen receptors of B cells, although all epitopes are not necessarily recognized with equal likelihood [Benjamin, et al.,*Ann. Rev. Immunol.*, 2:67 (1984)]. B cell epitopes of a protein are of two types: topographic and linear. The topographic type consists of amino acid residues which are spatially adjacent but may or may not be sequentially adjacent. The linear type consists of only sequentially adjacent residues. X-ray crystallographic data of Ag-Ab complexes indicate the size of their complementary binding region to have 16–17 amino acid residues [Amit, et al., *Science*, 233:747 (1986)], but peptide mapping suggests that less than about 8 residues contribute significantly to the binding process of a linear epitope [Appel, et al., *J. Immunol.*, 144:976 (1990)].

Allergens, like other protein antigens, can have both types of B cell epitopes or only one. For example, vespid antigen 5s have both types [King et al., *J. Immunol.*, 154:577 (1995)]. Bee venom melittin appears to have only one B cell epitope of linear type [King, et al., *J. Immunol.*, 133:2668 (1984)].

T cell epitopes of proteins consist of only the linear type since they are peptides that have been processed in the lysosomes of APC by proteases of unknown specificity [Unanue, *Curr. Op. Immunol.*, 4:63 (1992)]. Analysis of naturally processed antigenic peptides bound to MHC class II molecules indicates that their size ranges from about 13 to 17 amino acid residues, but analysis of synthetic peptide-MHC class II molecule complex for their T cell proliferate response suggests a minimal size of about 8 amino acid residues [Cf. Rudensky et al., *Nature*, 353:622 (1991)]. Studies suggest that T cell epitopes are distributed throughout the entire protein molecule, and they may function as major or minor determinants depending on the MHC haplotype of the immunized host [Roy, et al., *Science*, 244:572; Gammon, et al.,*Immunol. Rev.*, 98:53 (1987); O'Hehir et al., *Ann. Rev. Immunol.*, 9:67 (1991)].

Hypersensitivity of the immediate type is known to be caused by the presence of allergen-specific IgE. IgE is found in the circulation and bound to specific IgE-Fc receptors on mast cells and basophils. Cross-linking of cell-bound IgE by allergens leads to release of histamine, leukotrienes and other chemical mediators that cause the allergic symptoms. IgE is one of the different isotypes of immunoglobulins. As pointed out above, lymphokines secreted by T cells influence isotype switch events in B cells.

Because of the central role of TH2 cells in determining the isotypes switch event of B cells, the T cell epitopes of several allergens have been mapped [Cf. O'Hehir et al., supra]. These allergens include ragweed Amb a III, rye grass Lol p I, cat Fel d I, mouse urine Mus m I, midge Chi t I, bee venom phospholipase $A_2$ [Dhillon, et al., *J. Allergy Clin. Immunol.*, 90:42 (1992)] melittin [Fehlner, et al., *J. Immunol.*, 146:799 (1991)], and hornet antigen 5 [King et al., *J. Allergy Clin. Immunol.*, 91:283 (1993)]. The data do not reveal any unusual or common structural features. However, any conclusion from these data is qualified as these data are collected from humans and mice of different haplotypes.

Modulation of T and B Cell Responses

Normally hosts are tolerant to the dominant B and T cell epitopes of self proteins by clonal deletion and anergy. However this tolerance can be broken under certain circumstances [Gammon, et al., *Immunol. Today.,* 12: 93 (1991); Basten, et al., *Immunol. Rev.,* 122:5 (1991)]. It has been suggested that self-tolerance is broken in autoimmune diseases through encounters with foreign proteins that are similar to host proteins. Therefore the sequence similarity of allergens with autologous proteins is of interest for closer investigation.

Mature B cells are activated in response to multi-valent antigens which can cross-link cell surface Ig receptors [DeFranco. *Ann. Rev. Cell Biol.,* 3:143 (1987)], and they are rendered anergic in response to mono-valent antigen [Basten, et al., 1991, supra]. Antigen activation of T cells requires not only the integration of TCR with peptide-MHC complex but also with other co-stimulating signals on the surface of APC [Schwartz, *Science,* 248:1349 (1990); Jenkins and Miller, *FASEB J.,* 6:2428 (1992)]. Interaction of TCR with peptide-MHC complex in absence of co-stimulating signals can lead to T cell anergy.

The molecular mechanism of B or T cell anergy is not yet understood [Cf. Schwartz, 1990, supra; Jenkins and Miller, 1992, supra; Ales-Martinez, et al., *Immunol. Today,* 12:201 (1991)]. In vitro studies with T cell clones reveals that occupancy of TCR by artificial peptide-MHC complex in absence of co-stimulating signals leads to altered intracellular signal transduction and/or repressor gene activation which can prevent lymphokine transcription.

Early studies have shown that the physical state of the immunogen and the route of immunization are important variables in determining the outcome of an immune response. In the light of our current understanding, these variables may well influence antigen presentation so as to have T and B cell activation or anergy.

One way to treat allergic diseases is by immunotherapy which involves repeated subcutaneous injections of the offending allergen(s) into patients. The amounts of allergens which can be injected are limited by the danger of unwanted systemic allergic reaction in patients. For most patients following immunotherapy, their allergen-specific IgE levels initially rise followed with gradual decrease of their allergen-specific IgE levels, and there is also downregulation of allergen-specific T cell responses [P. S. Norman, *Current Op. Immunol.,* 5:968 (1993)].

Because of the undesirable systemic reaction on immunotherapy with native allergens, there has been continued interest in the development of modified allergens with reduced allergenic activities for imrnmunotherapy [T. P. King. in "Bronchial Asthma," edited by E. B. Weiss and M. Stein, Little Brown, Boston, pp. 43–49 (1993); R.E. O'Hehir et al., 1991, supra].

Three reports have appeared recently on the use of T cell epitope peptides to modulate allergen-specific immune responses. One report is on the subcutaneous injection of mice with two peptides from the major cat allergen Fel d I to decrease T cell response to the entire molecule Fel d I [Briner et al., *Proc. Natl. Acad. Sci. U.S.A.,* 90:7608–12 (1993)]. Another is on the intranasal therapy with a peptide from the major mite allergen Der p I to suppress allergen-specific response in naive or sensitized mice [Hoyne et al., *J. Exp. Med.,* 178:1783–1788 (1993)]. The third reports that peptides containing T cell epitopes of bee venom phospholypase $A_2$ were used successfully in immunotherapy to treat patients with bee venom allergy [Müller et al., *J. Allergy Clin. Immunol.* 97:426 (1996)].

Since an MHC class II molecule of any one haplotype can bind a wide range of peptides in its binding groove, it may Pe possible to modulate T cell response by inhibition of allergen-derived T cell epitope binding to MHC molecules with other peptides. For example, a mouse lysozyme peptide which is not immunogenic by itself in $H-2^k$ mice inhibits T cell response to hen egg white lysozyme [Adorini and Nagy, *Immunol. Today.,* 11:21 (1990)]. Another example is the in vitro inhibition of T cell response to a mite allergen by an influenza HA peptide [O'Hehir et al., *J. Allergy Clin. Immunol.,* 87:1120 (1991)].

Experimental autoimmune encephalomyelitis (EAE) in mice or rats is a well-studied model for multiple sclerosis. Many studies have identified immunodominant T cell determinants for myelin basic protein, which is used to induce this condition. Peptides that correspond to immunodominant epitopes of myelin basic protein can induce tolerance to the same peptide antigen or to the intact myelin basic protein. The same peptides that induced tolerance could also induce T cell anergy in an ongoing autoinmmune response [Gaur et al., *Science,* 259:1491–1494 (1992)].

It has been reported that subcutaneous or intranasal pretreatment of mice with T cell epitopes peptides of the major cat allergen Fel d 1 [Briner et al., *Proc. Natl. Acad. Sci. USA,* 90:7608–7612 (1993)] or the major mite allergen Der p 1 [Hoyne et al., *J. Exp. Med.,* 178:1783–1788 (1993)] lead to T cell anergy and that reduced antibody responses are observed on subsequent immunization with the allergen. T cell epitope peptides of Fel d 1 studied in the murine system are currently being evaluated for immunotherapy of patients [Norman et al., *J. Allergy Clin. Immunol.,* 95:259 (1995)]. Published data indicate that the T cell epitope regions of Der p 1 detected in the murine system overlap those found in humans [O'Hehir et al., *Eruop. J. Clin. Invest.,* 23:763 (1993)]. On the basis of findings with Fel d 1 and Der p 1, it is reasonable to conclude that the T cell epitope data of white faced hornet Ag5 obtained in mice as described herein will be applicable for studies in humans.

There remains a need in the art for the identification of T cell epitopes of vespid venom allergens, particularly antigen 5, for immunotherapy of venom allergy.

There is also a need in the art to use peptides having T cell epitopes of vespid venom allergens to study induction of tolerance in mice and induction of tolerance in humans.

There is a further need to test whether a modified peptide inhibits allergen T cell epitope binding to MHC class II molecule, or induces T cell anergy, or both.

These and other needs in the art are satisfied by the present invention.

The citation of references herein shall not be construed as an admission that such is prior art to the present invention.

SUMMARY OF THE INVENTION

The present invention provides the sequences of immunodominant peptides of vespid venom antigen 5, and corresponding peptides from other antigens, such as fire ant Sol i 3. An immunodominant peptide is one that contains a T cell epitope of the antigen, such that T cells immunized with the antigen will be stimulated when contacted with the peptide. Such peptides of the invention are preferably immunomodulatory peptides as well, in that they induce T cell anergy when administered to a subject, or otherwise affect the immune response of the subject.

In yet another embodiment, the present invention provides a pharmaceutical composition effective for the treatment of a vespid venom allergen-specific allergic condition comprising a polypeptide of the invention that has an immunomodulatory portion of a T cell epitope of a vespid venom antigen 5. More particularly, the invention provides pharmaceutical compositions comprising such polypeptides, including different isoforms, of a vespid venom antigen 5, for example, *Dolichovespula maculata, Vespula vulgaris, Vespula maculifrons, Dolichovespula arenaria, Polistes annularis,* and *Polistes exclamans.*

In yet still another embodiment, the present invention provides a method for treating a vespid venom allergen-specific condition comprising administering a therapeutically effective dose of a pharmaceutical composition of the invention.

In its broadest aspect, the present invention is directed to a peptide characterized by having between 8 (the generally recognized minimum number of amino acids for an antigenic T cell epitope) and 35 amino acid residues of vespid venom antigen 5; and being antigenic for T cell proliferation in a mouse immunized with a vespid venom antigen 5, which mouse is a strain selected from the group consisting or BALB/c, ASW/Sn, C3H/He, and P/J. More particularly, a peptide of the invention corresponds to a fragment of white face hornet antigen 5, form 2, selected from the group consisting of:

| | |
|---|---|
| NNYCKIKCRKGIHTLCKFGT; | (SEQ ID NO:8) |
| GIHTLCKFGTSMKPNCGRNV; | (SEQ ID NO:9) |
| KNEILKRHNDFRQNVAKGLE; | (SEQ ID NO:12) |
| FRQNVAKGLETRGKPGPQPP; | (SEQ ID NO:13) |
| TRGKPGPQPPAKNMNVLVWN; | (SEQ ID NO:14) |
| DELAKIAQTWANQCDFNHDD; | (SEQ ID NO:16) |
| CRNTAKYQVGQNIAISSTTA; | (SEQ ID NO:18) |
| QNIAISSTTATQFDRPSKLI; | (SEQ ID NO:19) |
| TQFDRPSKLIKQWEDEVTEF; | (SEQ ID NO:20) |
| KQWEDEVTEFNYKVGLQNSN; | (SEQ ID NO:21) |
| NYKVGLQNSNFRKVGHYTQM; | (SEQ ID NO:22) |
| FRKVGHYTQMVWGKT; | (SEQ ID NO:23) |
| KEIGCGSIKYIEDNWYTHYL; and | (SEQ ID NO:25) |
| IEDNWYTHYLVCNYGPGGND. | (SEQ ID NO:26) |

Such peptides may be from the specific antigen, white face hornet antigen 5, form 2, or may be from the corresponding segments of other vespid venom antigens, such as but not limited to *Dolichovespula maculata, Vespula vulgaris, Vespula maculifrons, Dolichovespula arenaria,* and *Polistes exclamans.* Other sources of antigen 5 of the invention include *Vespa crabo* (European hornet), *V. flavopilosa* (yellow jacket), *V. germanica* (yellowjacket), *V. pennsylvannica* (yellowjacket), *V. squamosa* (yellowjacket), *V. vidue* (yellowjacket), and *P fuscatus* (paperwasp), or fire ant allergen Sol i 3, which shares sequence similarity with (and possibly is homologous to) vespid venom antigen 5s. Such corresponding peptides from various species are referred to herein as homologs, as they represent variants from the corresponding, i.e., homologous, alleles of the antigen 5 gene from different vespid species. The term allelic variant includes, as well, single amino acid variations in antigen 5s from the same species, including different isoforms (such as the three isoforms found for white face hornet antigen 5), and mutations.

Preferably, the peptide corresponds to a fragment of white face hornet antigen 5, form 2, selected from the group consisting of:

| | |
|---|---|
| NNYCKIKCRKGIHTLCKFGT; | (SEQ ID NO:8) |
| GIHTLCKFGTSMKPNCGRNV; | (SEQ ID NO:9) |
| KNEILKRHNDFRQNVAKGLE; | (SEQ ID NO:12) |
| FRQNVAKGLETRGKPGPQPP; | (SEQ ID NO:13) |
| DELAKIAQTWANQCDFNHDD; | (SEQ ID NO:16) |
| NYKVGLQNSNFRKVGHYTQM; | (SEQ ID NO:22) |
| FRKVGHYTQMVWGKT; and | (SEQ ID NO:23) |
| IEDNWYTHYLVCNYGPGGND. | (SEQ ID NO:26) |

This group of peptides showed significant T cell stimulation of antigen 5-immunized T cells in more than one species.

As pointed out above, the present invention advantageously provides not only the immunodominant T cell epitopes for white face hornet antigen 5, but corresponding epitopes from antigen 5s from other vespid species, particularly subfamilies Vespinae and Polistinae, more particularly the genera Vespa, Vespula, Dolichovespula, and Polistes. In addition, the invention provides for consensus polypeptides, which incorporate the same amino acid residues at conserved positions, and any amino acid residue or amino acid residues having similar properties at divergent positions. In other words, the present invention contemplates immunodominant peptides that incorporate polymorphisms found among the antigen 5 homologs from different species.

In a specific embodiment, the peptide has the amino acid sequence $X_1BYCKIX_2CX_3X_4GX_5X_6HTX_7CX_8X_9G$ (SEQ ID NO:31), wherein $X_1$ is a neutral amino acid residue, $X_2$ is a basic amino acid residue or deleted, $X_3$ is any amino acid residue, $X_4$ is a polar amino acid, $X_5$ is glycine or deleted, $X_6$ is any amino acid residue, $X_7$ is an amino acid residue with an aliphatic side chain, $X_8$ is a polar amino acid residue, and $X_9$ is an amino acid residue with an aromatic side chain. In a more specific embodiment, $X_1$ is valine or asparagine; $X_2$ is lysine, arginine, or deleted; $X_3$ is proline, arginine, serine, or leucine; $X_4$ is arginine, lysine, or serine; $X_6$ isoleucine, leucine, threonine, or valine; $X_7$ is alanine, valine, isoleucine, or leucine; $X_8$ is lysine, arginine, glutamine, or asparagine: or $X_9$ is plienylalanine, tryptophan, or tyrosine; or any combination of the foregoing.

In another specific embodiment, the peptide has the amino acid sequence $GX_5X_6HTX_7CX_8X_9GX_{10}SX_{11}KPX_{12}X_{13}NCX_{14}X_{15}X_{16}X_{17}X_{18}$ (SEQ ID NO:32), wherein $X_5$ is glycine or deleted, $X_6$ is any amino acid residue, $X_7$ is an amino acid residue with an aliphatic side chain, $X_8$ is a polar amino acid residue, $X_9$ is an amino acid residue with an aromatic side chain, $X_{10}$ is a polar amino acid residue, $X_{11}$ is any amino acid residue, $X_{12}$ is a polar amino acid residue or deleted, $X_{13}$ is a basic amino acid residue or deleted, $X_{14}$ is a small chain amino acid residue, $X_{15}$ is any amino acid residue, $X_{16}$ is a basic or polar neutral amino acid residue, $X_{17}$ is any amino acid residue, and $X_{18}$ is an aliphatic amino acid residue. More specifically, $X_6$ is isoleucine, leucine, threonine, or valine; $X_7$ is alanine, valine, isoleucine, or leucine; $X_8$ is lysine, arginine, glutamine, or asparagine; $X_9$ is phenylalanine, tryptophan, or tyrosine; $X_{10}$ is threonine, serine, aspartic acid, or glutamic acid; $X_{11}$ is leucine, isoleucine, methionine, or threonine; $X_{12}$ is serine or deleted; $X_{13}$ is lysine, arginine, or deleted; $X_{14}$ is glycine or alanine; $X_{15}$ is asparagine, glutamine, glycine, serine, arginine, or lysine; $X_{16}$ is lysine, arginine, asparagine, or glutamine; $X_{17}$ is lysine, arginine, isoleucine, leucine, or valine; or $X_{18}$ is alanine, valine, isoleucine, or leucine; or any combination of the foregoing.

The present invention also advantageously provides for combining two overlapping peptides into a larger peptide having up to 35 amino acid residue. In one such embodiment, the peptide has the amino acid sequence $X_1BYCKIX_2CX_3X_4GX_5X_6HTX_7CX_8X_9GX_{10}SX_{11}KPX_{12}X_{13}NCX_{14}X_{15}X_{16}X_{17}X_{18}$ (SEQ ID NO:33), wherein $X_1$ is a neutral amino acid residue, $X_2$ is a basic amino acid residue or deleted, $X_3$ is any amino acid residue, $X_4$ is a polar amino acid, $X_5$ is glycine or deleted, $X_6$ is any amino acid residue, $X_7$ is an amino acid residue with an aliphatic side chain, $X_8$ is a polar amino acid residue, $X_9$ is an amino acid residue with an aromatic side chain, $X_{10}$ is a polar amino acid residue, $X_{11}$ is any amino acid residue, $X_{12}$ is a polar amino acid residue or deleted, $X_{13}$ is a basic amino acid residue or deleted, $X_{14}$ is a small chain amino acid residue, $X_{15}$ is any amino acid residue, $X_{16}$ is a basic or polar neutral amino acid residue, $X_{17}$ is any amino acid residue, and $X_{18}$ is an aliphatic amino acid residue. In a more specific embodiment, $X_1$ is valine or asparagine; $X_2$ is lysine, arginine, or deleted; $X_3$ is proline, arginine, serine, or leucine; $X_4$ is arginine, lysine, or serine; $X_6$ isoleucine, leucine, threonine, or valine; $X_7$ is alanine, valine, isoleucine, or leucine; $X_8$ is lysine, arginine, glutamine, or asparagine; $X_9$ is phenylalanine, tryptophan, or tyrosine; $X_{10}$ is threonine, serine, aspartic acid, or glutamic acid; $X_{11}$ is leucine, isoleucine, methionine, or threonine; $X_{12}$ is serine or deleted; $X_{13}$ is lysine, arginine, or deleted; $X_{14}$ is glycine or alanine; $X_{15}$ is asparagine, glutamine, glycine, serine, arginine, or lysine; $X_{16}$ is lysine, arginine, asparagine, or glutamine; $X_{17}$ is lysine, arginine, isoleucine, leucine, or valine; or $X_{18}$ is alanine, valine, isoleucine, or leucine; or any combination of the foregoing.

In another specific embodiment, the peptide has the amino acid sequence $KX_{19}X_{20}IX_{21}X_{22}X_{23}HNX_{24}FRQKX_{25}AX_{26}GLE$ (SEQ ID NO:34), wherein $X_{19}$ is a basic or neutral polar amino acid residue $X_{20}$ is any amino acid residue $X_{21}$ is an aliphatic amino acid residue, $X_{22}$ is a polar amino acid residue, $X_{23}$ is a polar charged amino acid residue, $X_{24}$ is a polar amino acid residue, $X_{25}$ is an aliphatic amino acid residue; and $X_{26}$ is a polar basic or neutral amino acid residue. More specifically, $X_{19}$ is asparagine, glutamine, or lysine; $X_{20}$ is aspartic acid, glutamic acids, leucine, or isoleucine; $X_{21}$ is valine, leucine, or isoleucine; $X_{22}$ arginine, asparagine, or serine; $X_{23}$ is glutamic acid or arginine; $X_{24}$ is aspartic acid, glutamic acid, asparagine, glutamine, or arginine; $X_{25}$ is valine, leucine, or isoleucine; or $X_{26}$ is arginine, asparagine, or lysine; or any combination of the foregoing.

In still another specific embodiment, the peptide has the amino acid sequence $FRQKX_{25}AX_{26}GLETRGX_{27}PGPQPX_{28}$ (SEQ ID NO:35), wherein $X_{25}$ is an aliphatic amino acid residue, $X_{26}$ is a polar basic or neutral amino acid residue, $X_{27}$ is a polar basic or neutral amino acid residue, and $X_{28}$ is any amino acid residue. More specifically, $X_{25}$ is valine, leucine, or isoleucine; $X_{26}$ is arginine, asparagine, or lysine; $X_{27}$ is asparagine or lysine; or $X_{28}$ is glycine, alanine, or proline; or any combination of the foregoing.

As noted above, overlapping peptides may be provided as a single, larger peptide. Thus, in another embodiment, the peptide has the amino acid sequence $KX_{19}X_{20}IX_{21}X_{22}X_{23}HNX_{24}FRQKX_{25}AX_{16}GLETRGX_{27}PGPQPX_{28}$ (SEQ ID NO:36), wherein $X_{19}$ is a basic or neutral polar amino acid residue $X_{20}$ is any amino acid residue $X_{21}$ is an aliphatic amino acid residue, $X_{22}$ is a polar amino acid residue, $X_{23}$ is a polar charged amino acid residue, $X_{24}$ is a polar amino acid residue, $X_{25}$ is an aliphatic amino acid residue, $X_{26}$ is a polar basic or neutral amino acid residue, $X_{27}$ is a polar basic or neutral amino acid residue, and $X_{28}$ is any amino acid residue. More specifically, $X_{19}$ is asparagine, glutamine, or lysine; $X_{20}$ is aspartic acid, glutamic acids, leucine, or isoleucine; $X_{21}$ is valine, leucine, or isoleucine; $X_{22}$ arginine, asparagine, or serine; $X_{23}$ is glutamic acid or arginine; $X_{24}$ is aspartic acid, glutamic acid, asparagine, glutamine, or arginine; $X_{25}$ is valine, leucine, or isoleucine; $X_{26}$ is arginine, asparagine, or lysine; $X_{27}$ is asparagine or lysine; or $X_{28}$ is glycine, alanine, or proline; or any combination of the foregoing.

In yet another embodiment, the peptide has the amino acid sequence $DELAX_{29}X_{30}AQX_{31}WAX_{32}QCX_{33}X_{34}X_{35}X_{36}HD$ (SEQ ID NO:37), wherein $X_{29}$ is any amino acid residue, $X_{30}$ is an aliphatic amino acid residue, $X_{31}$ is any amino acid residue, $X_{32}$ is a polar neutral amino acid residue, $X_{33}$ is a polar neutral or acidic amino acid residue, $X_{34}$ is an aromatic amino acid residue, $X_{35}$ is an aliphatic amino acid residue or deleted, and $X_{36}$ is any amino acid residue. More specifically, $X_{29}$ is tyrosine, lysine, or histidine; $X_{30}$ is isoleucine, leucine, or valine; $X_{31}$ is threonine or valine; $X_{32}$ is serine or asparagine; $X_{33}$ is glutamine, asparagine, aspartic acid, or serine; $X_{34}$ is phenylalanine to tyrosine; $X_{35}$ is isoleucine, leucine, or deleted; or $X_{36}$ is glycine, asparagine, or valine; or any combination of the foregoing.

In still another specific embodiment, the peptide has the amino acid sequence $NX_{37}X_{38}X_{39}X_{40}X_{41}X_{42}X_{43}X_{44}BX_{45}FX_{46}KX_{47}GHYTQM$ (SEQ ID NO:38), wherein $X_{37}$ is a cyclic amino acid residue, $X_{38}$ is a polar basic or neutral amino acid residue, $X_{39}$ is any amino acid residue, $X_{40}$ is any amino acid residue, $X_{41}$ is a non-polar amino acid residue, $X_{42}$ is any amino acid residue, $X_{43}$ is a polar amino acid residue or glycine, $X_{44}$ is a polar basic or neutral amino acid residue, $X_{45}$ is a polar neutral amino acid or deleted, $X_{46}$ is any amino acid residue, and $X_{47}$ is a non-polar amino acid residue. More specifically, $X_{37}$ is proline or tyrosine; $X_{38}$ is asparagine, arginine, or histidine; $X_{39}$ is lysine, threonine, or valine; $X_{40}$ is aspartic acid, glycine, or lysine; $X_{41}$ is isoleucine, leucine, phenylalanine, or threonine; $X_{42}$ is glutamine, isoleucine, leucine, methionine, serine, or threonine; $X_{43}$ is asparagine, glutamic acid, histidine, lysine, or glycine, $X_{44}$ is aspartic acid, asparagine, glutamine, or serine; $X_{45}$ is asparagine or deleted, $X_{46}$ is alanine, arginine, leucine, isoleucine, or serine; or $X_{47}$ is isoleucine, leucine, threonine, or valine; or any combination of the foregoing.

In still another embodiment, the peptide has the amino acid sequence $FX_{46}KX_{47}GHYTQMVWX_{48}X_{49}T$ (SEQ ID NO:39), wherein $X_{46}$ is any amino acid residue. $X_{47}$ is a non-polar amino acid residue, $X_{48}$ is a small side chain amino acid residue, and $X_{49}$ is a polar basic or neutral amino acid residue. More specifically, $X_{46}$ is alanine, arginine, leucine, isoleucine, or serine; $X_{47}$ is isoleucine, leucine, threonine, or valine; $X_{48}$ is glycine or alanine; or $X_{49}$ is lysine or asparagine; or any combination of the foregoing.

In another embodiment of the invention wherein two overlapping peptides are combined, the peptide has the amino acid sequence $NX_{37}X_{38}X_{39}X_{40}X_{41}X_{42}X_{43}X_{44}BX_{45}FX_{46}KX_{47}GHYTQMVWX_{48}X_{49}T$ (SEQ ID NO:40), wherein $X_{37}$ is a cyclic amino acid residue, $X_{38}$ is a polar basic or neutral amino acid residue, $X_{39}$ is any amino acid residue, $X_{40}$ is any amino acid residue, $X_{41}$ is a non-polar amino acid residue, $X_{42}$ is any amino acid residue, $X_{43}$ is a polar amino acid residue or glycine, $X_{44}$ is a polar basic or neutral amino acid residue, $X_{45}$ is a polar neutral amino acid or deleted, $X_{46}$ is any amino acid residue, $X_{47}$ is a non-polar amino acid residue, $X_{48}$ is a small side chain amino acid residue, and $X_{49}$ is a polar basic or neutral amino acid residue. More specifically, $X_{37}$ is proline or tyrosine, $X_{38}$ is asparagine, arginine, or histidine; $X_{39}$ is lysine, threonine, or valine; $X_{40}$ is aspartic acid, glycine, or lysine; $X_{41}$ is isoleucine, leucine, phenylalanine, or threonine; $X_{42}$ is glutamine, isoleucine, leucine, methionine, serine, or threonine; $X_{43}$ is asparagine, glutamic acid, histidine, lysine, or glycine, $X_{44}$ is aspartic acid, asparagine, glutamine, or serine; $X_{45}$ is asparagine or deleted, $X_{46}$ is alanine, arginine, leucine, isoleucine, or serine; $X_{47}$ is isoleucine, leucine, threonine, or valine; $X_{48}$ is glycine or alanine; or $X_{49}$ is lysine or asparagine; or any combination of the foregoing.

In still another embodiment, the peptide has the amino acid sequence $X_{50}ZX_{51}X_{52}X_{53}X_{54}X_{55}HYLX_{56}CNYGPX_{57}GNX_{58}X_{59}X_{60}$ (SEQ ID NO:41), wherein $X_{50}$ is a non-polar amino acid, $X_{51}$ is a polar acidic or neutral amino acid residue, $X_{52}$ is a polar basic or neutral amino acid residue, $X_{53}$ is a non-polar amino acid residue, $X_{54}$ is a moderately polar amino acid residue, $X_{55}$ is a polar basic or neutral amino acid residue, $X_{56}$ is an aliphatic amino acid residue, $X_{57}$ is any amino acid residue, $X_{58}$ is any amino acid residue, $X_{59}$ is any amino acid residue, and $X_{60}$ is any amino acid residue. More specifically, $X_{50}$ is isoleucine, leucine, or methionine; $X_{51}$ is asparagine, aspartic acid, glutamine, or glutamic acid; $X_{52}$ is asparagine or lysine; $X_{53}$ is methionine or tryptophan; $X_{54}$ glutamine, histidine, or tyrosine; $X_{55}$ is asparagine, lysine, or threonine, $X_{56}$ isoleucine, leucine, or valine; $X_{57}$ is alanine, glycine, or serine; $X_{58}$ is aspartic acid, phenylalanine, or tyrosine; $X_{59}$ is glutaminie, leucine, isoleucine, methionine, or phenylalanine; or $X_{60}$ is asparagine, aspartic acid, or glycine; or any combination of the foregoing.

In specific embodiments, the invention is directed to a peptide having an amino acid sequence selected from the group consisting of:

NNYCKIKCRKGIHTLCKFGT (SEQ ID NO: 8), or its homolog;

GIHTLCKFGTSMKPNCGRNV (SEQ ID NO:9), or its homolog;

NNYCKIKCRKGIHTLCKFGTSMKPNCGRNV (SEQ ID NO:42), or its homolog;

KNEILKRHNDFRQNVAKGLE (SEQ ID NO:12), or its homolog;

FRQNVAKGLETRGKPGPQPP (SEQ ID NO:13), or its homolog;

KNEILKRHNDFRQNVAKGLETRGKPGPQPP (SEQ ID NO:43), or its homolog;

DELAKIAQTWANQCDFNHDD (SEQ ID NO:16), or its homolog;

NYKVGLQNSNFRKVGHYTQM (SEQ ID NO:22), or its homolog;

FRKVGHYTQMVWGKT (SEQ ID NO:23), or its homolog;

-continued

NYKVGLQNSNFRKVGHYTQMVWGKT (SEQ ID NO:44), or its homolog; and

IEDNWYTHYLVCNYGPGGND (SEQ ID NO:26), or its homolog;

In specific embodiments, infra, peptides having SEQ ID NOS:8, 9, 12, 13, 16, 22, 23, and 26 are shown to be dominant in more than one strain of mouse.

In addition to homologous variants, allelic variant, consensus variant, and combined variant peptides of the invention, the present invention further provides a recombinant polypeptide comprising two or more peptides non-contiguously arranged relative to the native sequence of vespid venom antigen 5. Although the term recombinant generally refers to polypeptides generated by genetic engineering, which meaning is fully intended according to the present invention, the term recombinant is used herein more generally, to refer to polypeptides created by combination (or recombination) of non-contiguous immunodominant peptide fragment of vespid venom antigen 5. Such fragments may be from antigen 5 from the same species, antigen 5 peptides from different species, consensus antigen 5 peptides as described above, or any combination of the foregoing. In a specific embodiment, the peptides are selected from the group consisting of:

NNYCKIKCRKGIHTLCKFGT (SEQ ID NO: 8), or its homolog;

GIHTLCKFGTSMKPNCGRNV (SEQ ID NO:9), or its homolog;

NNYCKIKCRKGIHTLCKFGTGTSMKPNCGRNV (SEQ ID NO:42), or its homolog;

KNEILKRHNDFRQNVAKGLE (SEQ ID NO:12), or its homolog;

FRQNVAKGLETRGKPGPQPP (SEQ ID NO:13), or its homolog;

KNEILKRHNDFRQNVAKGLETRGKPGPQPP (SEQ ID NO:43), or its homolog;

DELAKIAQTWANQCDFNHDD (SEQ ID NO:16), or its homolog;

NYKVGLQNSNFRKVGHYTQM (SEQ ID NO:22), or its homolog;

FRKVGHYTQMVWGKT (SEQ ID NO:23), or its homolog;

NYKVGLQNSNFRKVGHYTQMVWGKT (SEQ ID NO:44), or its homolog; and

IEDNWYTHYLVCNYGPGGND (SEQ ID NO:26), or its homolog;

In specific embodiments, the present invention is directed to the following homologous T cell peptides of hornet Ag5 from two species each of hornet (Dol a and Dol m), yellowjacket (Ves m and Ves v) and wasp (Pol a and Pol e) and one species of fire ant (Sol i) shown in Table 2. As noted above, there are two forms of Dol m 5.01 and 5.02, referred to as Dol m A and B here. Residues given below refer to Dol m 5.02 numbering, and gaps are added to obtain maximal sequence alignment. Where immunodominant peptides overlap, the fragment containing the overlapping sequences are provided, with the specific sequences demarcated by a line under the peptide group. In such specific embodiments, the present invention contemplates both the individual immunodominant peptides and the larger peptide containing the overlapping segments.

TABLE 2

Homologs of Immunodominant Peptides

Peptides 1 and 2 (residue 1–20 and 11–30)

| | | | | | | |
|---|---|---|---|---|---|---|
| Ves m | NNYCKI | KCLKGG | VHTACKYG | SLKP | NCGNKkV | SEQ ID NO: 45 |
| Ves v | NNYCKI | KCLKGG | VHTACKYG | SLKP | NCGNKvV | SEQ ID NO: 46 |
| Dol a | NNYCKI | CpKG | tHTLCKYGTSMKP | | NCGgKIVK | SEQ ID NO: 47 |
| Dol mA | NNYCKI | KCsrG | IHTLCKFGTSMKP | | NCGsKIVK | SEQ ID NO: 48 |
| Dol mB | NNYCKI | KCrkG | IHTLCKFGTSMKP | | NCGrnVVK | SEQ ID NO: 49 |
| Pol a | VDYCKI | KCPSG | IHTVCQYGESTKPSKNCAGKVIK | | | SEQ ID NO: 50 |
| Pol e | VDYCKI | KCPSG | IHTVCQYGESTKPSKNCAGKVIK | | | SEQ ID NO: 51 |
| Sol i | YNYCNLQSCKRNNAIHTMCQY | | TSPTPGPMCLEYSN | | | SEQ ID NO: 52 |

```
        1
                2
               2a
```

Peptides 5 and 6 (residue 41–60 and 51–70)

| | | |
|---|---|---|
| Ves m | KQDILKEHNDFRQKIARGLETRGNPGPQPPA | SEQ ID NO: 53 |
| Ves v | KQDILKEHNDFRQKIARGLETRGNPGPQPPA | SEQ ID NO: 54 |
| Dol a | KNEIVKRHNEFRQKVAqGLETRGNPGPQPPA | SEQ ID NO: 55 |
| Dol mA | KNEIVnRHNQFRQKVAKGLETRGNPGPQPPA | SEQ ID NO: 56 |
| Dol mB | KNEIlkRHNDFRQnVAKGLETRGkPGPQPPA | SEQ ID NO: 57 |
| Pol a | KKLIVSEHNRFRQKVAQGLETRGNPGPQPAA | SEQ ID NO: 58 |
| Pol e | KKLIVSEHNRFRQKVAQGLETRGNPGPQPAA | SEQ ID NO: 59 |
| Sol i | KDAIVNKHNELRQRVASGKEMRGTNGPQPPA | SEQ ID NO: 60 |

```
        5
                6
```

Peptide 9 (residue 81–100)

| | | | |
|---|---|---|---|
| Ves m | DELAYiAQVWANQCQY | GHDT | SEQ ID NO:61 |
| Ves v | DELAYvAQVWANQCQY | GHDT | SEQ ID NO:62 |
| Dol a | DELAKIAQTWANQCnF | GHDQ | SEQ ID NO:63 |
| Dol mA | DELAKIAQTWANQCsF | GHDQ | SEQ ID NO:64 |
| Dol mB | DELAKIAQTWANQCdF | nHDD | SEQ ID NO:16 |
| Pol a | DELAHIAQVWASQCQFL | VHDK | SEQ ID NO:65 |
| Pol e | DELAHIAQVWASQCQFL | VHDK | SEQ ID NO:66 |
| Sol i | PELATIAQRWANQCTE | EHDA | SEQ ID NO:67 |

```
        9
```

Peptide 15 and 20 (residue 141–160 and 151–165)

| | | | |
|---|---|---|---|
| Ves m | NPKKKFSeNn | FLKiGHYTQMVWANT | SEQ ID NO: 68 |
| Ves v | NPKKKFSgNd | FLKtGHYTQMVWANT | SEQ ID NO: 69 |
| Dol a | NPhKdlmhNN | FSKVGHYTQMVWGKT | SEQ ID NO: 70 |
| Dol mA | NPKKGtigdnn | FSKVGHYTQMVWGKT | SEQ ID NO: 71 |
| Dol mB | NYKvGlqnsN | FrKVGHYTQMVWGKT | SEQ ID NO: 44 |
| Pol a | NYNTGITKQN | FAKIGHYTQMVWGKT | SEQ ID NO: 72 |
| Pol e | NYNTGITKQN | FAKIGHYTQMVWGKT | SEQ ID NO: 73 |
| Sol i | NYNTGISFPSDDNILMKVEHYTQIVWAKT | | SEQ ID NO: 74 |

```
        15
               20
```

Peptide 18 (residue 176–195)

| | | |
|---|---|---|
| Ves m | IQEnWHKHYLVCNYGPSGNF | SEQ ID NO: 75 |
| Ves v | IQEKWHKHYLVCNYGPSGNF | SEQ ID NO: 76 |
| Dol a | IENKWHTHYLVCNYGPAGNY | SEQ ID NO: 77 |
| Dol mA | IENNWHTHYLVCNYGPAGNY | SEQ ID NO: 78 |
| Dol mB | IEdNWyTHYLVCNYGPgGNd | SEQ ID NO: 26 |
| Pol a | mENNMQNHYLICNYGPAGNY | SEQ ID NO: 79 |
| Pol e | iENkMQNHYLICNYGPAGNY | SEQ ID NO: 80 |
| Sol i | EPDNWTKHYLVCNYGPAGNV | SEQ ID NO: 81 |

The present invention further provides a pharmaceutical composition for treating vespid venom sensitivity, preferably where sensitivity to antigen 5 has been demonstrated, comprising any of the foregoing peptides of the invention and a pharmaceutically acceptable carrier. In a preferred aspect, the pharmaceutical composition comprises more than one peptide of the invention, thus greatly increasing the breadth of its effectiveness.

The invention naturally extends as well to a method for treating sensitivity to vespid venom comprising administering to a vespid venom allergic patient a therapeutically effective amount of a pharmaceutical composition of the invention. Preferably, the patient has been identified as sensitive to vespid venom antigen 5.

As demonstrated herein, the peptides of the invention are cross-reactive for a native testes protein. Thus, an important advance of the present invention is that it provides peptides specific for treatment of antigen 5-sensitive patients, regardless of the cause of this antigen 5 sensitivity In other words, as demonstrated herein, whether a subject develops antigen 5 sensitivity from vespid stings, fire ant bites, or to testes protein, the peptides of the present invention provide an advantageous therapeutic agent for treating such sensitivity.

Thus, a primary object of the present invention is to provide immunodominant peptides from vespid venom antigen 5.

A corollary object is to provide such immunodominant peptides that produce T cell anergy in subjects sensitive or allergic to vespid venom antigen 5.

Yet another object of the invention is to provide combinations of such immunodominant peptides for a broad treatment of vespid venom sensitive patients from a wide variety of MHC (HLA) backgrounds.

Still another object of the invention is to provide consensus immunodominant T cell epitopes of vespid venom antigen 5s.

These and other objects of the present invention can be better appreciated by reference to the following drawings, the Detailed Description of the Invention, and the Examples.

| ABBREVIATIONS | |
|---|---|
| Ag5, Ag 5 | antigen 5 |
| *Dol m Dolichovespula maculata* | white face hornet |
| *Dol a D. arenaria* | yellow hornet |
| *Pol a Polistes annularis* | wasp |
| *Pol e P. exclamans* | wasp |
| *Ves m Vespula maculifrons* | yellowjacket |
| *Ves v V. vulgaris* | yellowjacket |
| n-, r- | natural, recombinant (respectively) |
| PCR | polymerase chain reaction |
| TCR | T cell receptor for antigen |
| tpx | testes protein |

BRIEF DESCRIPTION OF THE DRAWINGS

FIG. 1. Amino acid sequence of vespid antigen 5s. Antigen 5s were isolated from yellowjackets (*Vespula maculifrons* and *vulgaris*), hornets (*Dolichovespula areniaria* and *maculata*) and wasps (*Polistes annularis* and *exclamans*). The sequences given are in the order of Ves m V, Ves v V, Dol a V, Dol m VA and VB, Pol a V, and Pol e V respectively. Residues which are common to all sequences are given on separate lines beneath the sequences; residues underlined or dotted represent conserved or variable regions, respectively.

FIG. 2. Peptide fragments of Dol m Antigen 5.2.

FIG. 3. Sequence similarity of hornet Ag5 and mouse and human tpx's. Bold characters indicate those residues of human and iuouse tpx's which are identical with those of Ag5. The underlines regions of greater than 7 residues in length have greater than 67% sequence identity, and each is interspersed with fewer than 4 substituted residues.

FIG. 4. Stimulation index profile of BALB/c mice spleens after 4 immunizations with natural (n)-Ag5. In vitro proliferation assays were performed with peptides at three concentrations: $1\times10^{-5}$M (open bar), $1.25\times10^{-6}$M ("uphill" hatch), and $1.56\times10^{-7}$M ("downhill" hatch). The corresponding concentrations of recombinant antigen 5 control were $1.0\times10^{-6}$M, $1.25\times10^{-7}$, and $1.56\times10^{-8}$M. The blank was 2200 cpm.

FIG. 5. Stimulation index profile of BALB/c mice spleens after 4 immunizations with recombinant (r)-Ag5. In vitro proliferation assays were performed with peptides at three concentrations: $1\times10^{-5}$M (open bar), $1.25\times10^{-6}$M ("uphill" hatch), and $1.56\times10^{-7}$M ("downhill" hatch). The corresponding concentrations of recombinant Antigen 5 were $1.0\times10^{-6}$M, $1.25\times10^{-7}$, and $1.56\times10^{-8}$M. The blank was 4700 cpm.

FIG. 6. Stimulation index profile of BALB/c mice spleens after 4 immunizations with r-Ag5. In vitro proliferation assays were performed with peptides at three concentrations: $1\times10^{-5}$M (open bar), $1.25\times10^{-6}$M ("uphill" hatch), and $1.56\times10^{-7}$M ("downhill" hatch). The corresponding concentrations of recombinant Antigen 5 were $1.0\times10^{-6}$M, $1.25\times10^{-7}$, and $1.56\times10^{-8}$M. The blank was 3970 cpm.

FIG. 7. Stimulation index profile of BALB/c mice spleens after 4 immunizations with r-frag IN (residue 1-114 of antigen 5). In vitro proliferation assays were performed with peptides at three concentrations: $1\times10^{-5}$M (open bar), $1.25\times10^{-6}$M ("uphill" hatch), and $1.56\times10^{-}$M ("downhill" hatch). The corresponding concentrations of recombinant Antigen 5 were $1.0\times10^{-6}$M, $1.25\times10^{-7}$, and $1.56\times10^{-8}$M. The blank was 4690 cpm.

FIG. 8. Stimulation index profile of BALB/c mice spleens after 4 immunizations with r-frag C (residue 151-204 of antigen 5). In vitro proliferation assays were performed with peptides at three concentrations: $1\times10^{-5}$M (open bar), $1.25\times10^{-6}$M ("uphill" hatch), and $1.56\times10^{-7}$M ("downhill" hatch). The corresponding concentrations of recombinant Antigen 5 were $1.0\times10^{-6}$M, $1.25\times10^{-7}$, and $1.56\times10^{-8}$M. The blank was 6620 cpm.

FIG. 9. Stimulation index profile of BALB/c mice spleens after 5 immunizations with r-frag IN. In vitro proliferation assays were performed with peptides at three concentrations: $1\times10^{-5}$M (open bar), $1.25\times10^{-6}$M ("uphill" hatch), and $1.56\times10^{-}$M ("downhill" hatch). The corresponding concentrations of recombinant Antigen 5 were $1.0\times10^{-6}$M, $1.25\times10^{-7}$, and $1.56\times10^{-8}$M. The blank was 4410 cpm.

FIG. 10. Stimulation index profile of BALB/c mice spleens after 5 immunizations with r-frag C. In vitro proliferation assays were performed with peptides at three concentrations: $1\times10^{-5}$M (open bar), $1.25\times10^{-6}$M ("uphill" hatch), and $1.56\times10^{-7}$M ("downhill" hatch). The corresponding concentrations of recombinant Antigen 5 were $1.0\times10^{-6}$M, $1.25\times10^{-7}$and $1.56\times10^{-8}$M. The blank was 7520 cpm.

FIG. 11. Stimulation index profile of ASW/sn mice spleens after 5 immunizations with r-Ag5. In vitro proliferation assays were performed with peptides at three concentrations: $1\times10^{-5}$M (open bar), $1.25\times10^{-6}$M ("uphill" hatch), and $1.56\times10^{-7}$M ("downhill" hatch). The corresponding concentrations of recombinant Antigen 5 were $1.0\times10^{-6}$M, $1.25\times10^{-7}$, and $1.56\times10^{-8}$M. The blank was 5640 cpm.

FIG. 12. Stimulation index profile of P/J mice spleens after 5 immunizations with r-Ag5. In vitro proliferation assays were performed with peptides at three concentrations: $1\times10^{-5}$M (open bar), $1.25\times10^{-6}$M ("uphill" hatch), and $1.56\times10^{-7}$M ("downhill" hatch). The corresponding concentrations of recombinant Antigen 5 were $1.0\times10^{-6}$M, $1.25\times10^{-7}$, and $1.56\times10^{-8}$M. The blank was 1730 cpm.

FIG. 13. Stimulation index profile of C3H/He mice spleens after 5 immunizations with r-Ag5. In vitro proliferation assays were performed with peptides at three concentrations: $1\times10^{-5}$M (open bar), $1.25\times10^{-6}$M ("uphill" hatch), and $1.56\times10^{-7}$M ("downhill" hatch). The corresponding concentrations of recombinant Antigen 5 were $1.0\times10^{-6}$M, $1.25\times10^{-7}$, and $1.56\times10^{-8}$M. The blank was 3130 cpm.

FIG. 14. Stimulation index profile of CS7B1/6 mice spleens after 5 immunizations with r-Ag5. In vitro proliferation assays were performed with peptides at three concentrations: $1 \times 10^{-5}$M (open bar), $1.25 \times 10^{-6}$M ("uphill" hatch), and $1.56 \times 10^{-7}$M ("downhill" hatch). The corresponding concentrations of recombinant Antigen 5 were $1.0 \times 10^{-6}$M, $1.25 \times 10^{-7}$, and $1.56 \times 10^{-8}$M. The blank was 1050 cpm.

FIG. 15. Stimulation index profile of BALB/c mice spleen cells after 4 immunizations with Tpx-N. Stimulation was tested with peptide or protein at three different concentrations: Open bars—$1.0 \times 10^{-5}$M peptide or Frag IN, $2.5 \times 10^{-6}$M Tp X-N; "uphill" hatch—$1.25 \times 10^{-6}$M peptide or Frag IN. $3.13 \times 10^{-7}$M, Tpx-N; "downhill" hatch—$1.5 \times 10^{-7}$M peptide and Frag IN, $3.91 \times 10^{-8}$M Tpx-N; and stippled—$1.96 \times 10^{-8}$M Frag IN, $4.89 \times 10^{-9}$M Tpx-N. The blank was 7270 cpm.

FIG. 16. Stimulation index profile of BALB/c mice spleen cells after 4 immunizations with Tpx-C. Stimulation was tested with peptide or protein at three different concentrations: Open bars—$1 \times 10^{-5}$M peptide, $5 \times 10^{-6}$M Frag C or Tpx-C; "uphill" hatch—$1.25 \times 10^{-6}$M peptide; $6.25 \times 10^{-7}$M Frag C or Tpx-C; "downhill" hatch—$1.56 \times 10^{-7}$M peptide, $7.8 \times 10^{-8}$M Frag C, Tpx-C: and stippled—$9.75 \times 10^{-9}$M Frag-C or Tpx-C. The blank was 5110 cpm.

DETAILED DESCRIPTION OF THE INVENTION

Figure 4:
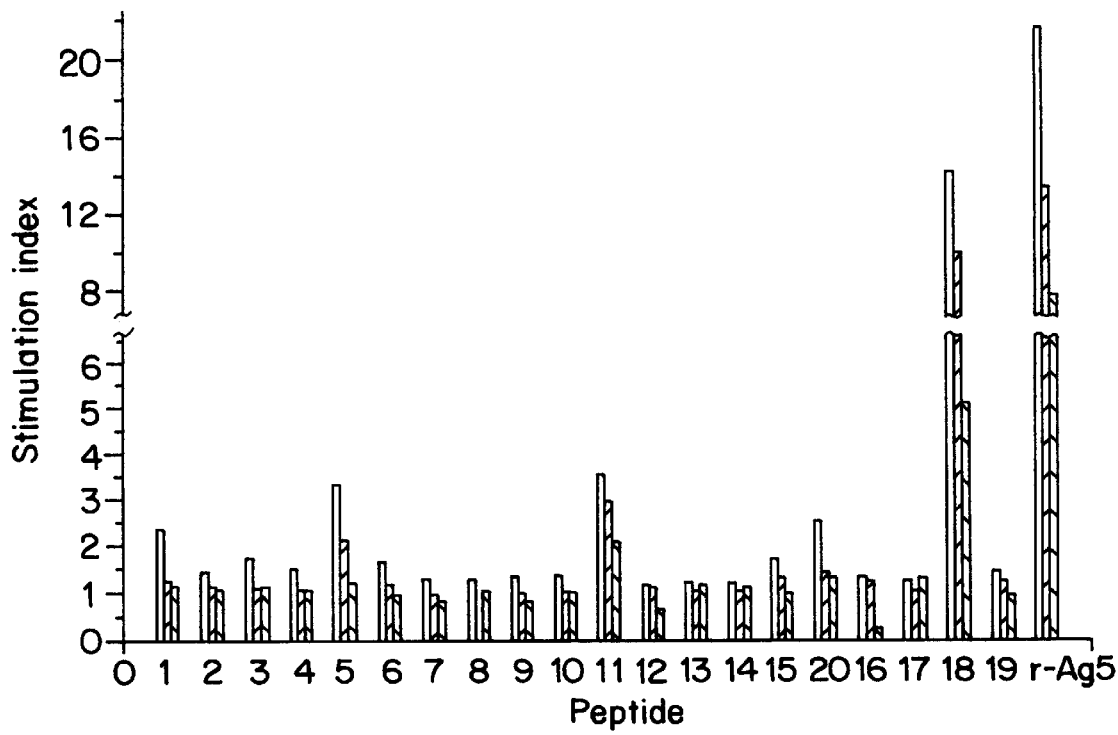

As noted above, the present invention provides the sequences of immunodominant peptides of vespid venom antigen 5, and corresponding peptides from other antigens, such as fire ant Sol i 3.

The term "immunodominant peptide" is used herein to refer to a peptide that contains a T cell epitope of the antigen, such that T cells immunized with the antigen will be stimulated when contacted with the peptide. The term T cell epitope is used herein in conformity with the definition in immunology. In one embodiment, an immunodominant epitope is an epitope that induces a greater than about 4-fold increase in stimulation of immunized T cells in an in vitro stimulation assay, particularly a greater than 2-fold, preferably greater than 4-fold, and more preferably greater than 6-fold increase in the stimulation index in a $^3$H-thymidine incorporation assay. In another embodiment, an immunodominant peptide is a peptide that induces proliferation or stimulation of different MHC-restricted populations of immunized T cells.

An immunodominant peptide of the invention may contain one epitope, or it may contain more than one epitope.

An immunomodulatory peptide" is a peptide that affects immune response in vivo. Preferably, an immunomodulatory peptide of the invention induces T cell anergy when administered to a subject.

The invention also provides pharmaceutical compositions effective for the treatment of a vespid venom allergen-specific allergic condition comprising a polypeptide of the invention, and methods for treating such allergic conditions comprising administering a therapeutically effective dose of the pharmaceutical compositions of the invention.

The polypeptides of the invention can also be useful for diagnosis of vespid venom-specific allergic conditions.

As used herein. the term "vespid venom allergen" refers to a protein found in the venom of a vespid, to which susceptible people are sensitized on exposure to the sting of the insect. While most antigens are characterized by being reactive with specific IgG class antibodies, an allergen is characterized by also being reactive with IgE type antibodies. The IgE type antibodies are responsible for mediating the symptoms of an allergic condition, i.e., immediate-type hypersensitivity. According to the invention, the vespid venom allergen of interest is vespid venom antigen 5.

As herein, the term "vespid" is used according to the practice of those in the field of allergy, and refers to insects belonging to the worldwide family of Vespidae, i.e., social wasps including hornets, yellowjackets, and paper wasps. In particular, vespids include the subfamilies *Vespinae* and *Polistinae*. More particularly, the vespids include the genera Vespa Linnaeus, Vespula Thomson, Dolichovespula Rohwer, and Polistes Latreille. Species in the genus Vespula include but are not limited to *V. germanica* (Fab.), *V. squamosa* (Drury), *V. maculifrons* (Buysson), *V. flavopilosa* (Jacobson), *V. vulgaris* (L.), and *V. pensylvannica* (Saussure). Species in the genus Polistes include but are not limited to *P. annularis* (Linnaeus), *P. exclamans* (Viereck), *P. metricus* (Say), *P. fuscatus* (Fabricius), and *P. apachus* (Saussure). Species in the genus Doliclovespula include but are not limited to *D. maculata* (L.) and *D. arenaria* (Fab.). Species in the genus Vespa include but are not limited to *V. crabro* (L.) and *V. orientalis* (Linnaeus).

As used herein, the term "immunomodulatory" refers to an ability to increase or decrease an antigen-specific immune response, either at the B cell or T cell level. Immunomodulatory activity can be detected e.g., in T cell proliferation assays, by measurement of antibody production, lymphokine production or T cell responsiveness. In particular, in addition to affects on T cell responses, the immunomodulatory polypeptides of the invention may bind to immunoglobulin (i.e., antibody) molecules on the surface of B cells, and affect B cell responses as well.

For the sake of clarity, the present invention is described in detail in sections relating to an immunomodulatory fragment of a vespid venom antigen 5, or derivatives and analogs of the vespid venom antigen 5, assays with the immunomodulatory vespid venom antigen 5, fragments, or derivatives or analogs thereof, and finally therapeutic and diagnostic uses of the vespid venom antigen 5 fragments, or derivatives or analogs thereof.

Immunodominant Peptides of Vespid Venom Ag5

An immunodominant peptide of the invention is a peptide comprising at least one T cell epitope, with a minimum size of approximately 8 amino acid residues (the minimum length generally regarded as requisite for antigen-specific recognition by a T cell). A peptide comprising at least one T cell epitope is capable of eliciting a T cell response. such as stimulation or T cell anergy (tolerization).

The immunodominant peptides of the invention have been identified in murine backgrounds. However, those peptides that are antigenic (comprise a T cell epitope) in more than one mouse strain are excellent candidates for immunodominant epitopes in antigen 5 sensitive humans. As pointed out above, on the basis of findings with Fel d 1 and Der p 1, it is reasonable to conclude that the T cell epitope data of a vespid venom antigen 5 found in mice, particularly in multiple strains, will be applicable for humans.

Also contemplated by the term "immunodominant peptide" are peptides which join two or more discontinuous epitopes (or the specific peptides disclosed herein) in a single polypeptide. In one aspect, such "aggregate" polypeptides can be prepared chemically, e.g., by crosslinking peptides, or using condensation techniques to form peptide bonds. Alternatively, synthetic DNA molecules encoding such aggregate peptides can be prepared, inserted in a recombinant expression vector, and the aggregate peptide expressed by host cells transformed or transfected with the expression vector and cultured under conditions that allow for expression of the aggregate polypeptide.

Immunodominant peptides of the invention can also be prepared as fusion proteins.

Amino acids used for peptide synthesis may be standard Boc ($N^\alpha$-amino protected $N^\alpha$-t-butyloxycarbonyl) amino acid resin with the standard deprotecting, neutralization, coupling and wash protocols of the original solid phase procedure of Merrifield [1963, *J. Am. Chem. Soc.* 85:2149–2154], or the base-labile $N^\alpha$-amino protected 9-fluorenylmethoxycarbonyl (Fmoc) amino acids first described by Carpino and Han [1972, *J. Org. Chem.* 37:3403–3409]. Both Fmoc and Boc $N^\alpha$-amino protected amino acids can be obtained from Fluka, Bachem, Advanced Chemtech, Sigma, Cambridge Research Biochemical, Bachem, or Peninsula Labs or other chemical companies familiar to those who practice this art. In addition, the method of the invention can be used with other $N^\alpha$-protecting groups that are familiar to those skilled in this art. Solid phase peptide synthesis may be accomplished by techniques familiar to those in the art and provided, for example, in Stewart and Young, 1984, Solid Phase Synthesis, Second Edition, Pierce Chemical Co., Rockford, Ill.; Fields and Noble, 1990, Int. J. Pept. Protein Res. 35:161–214, or using automated synthesizers, such as sold by ABS.

Alternatively, immunodominanit peptides of the invention can be prepared by recombinant DNA techniques. Thus, in accordance with the present invention there may be employed conventional molecular biology, microbiology, and recombinant DNA techniques within the skill of the art. Such techniques are explained fully in the literature [see, e.g., Sambrook, Fritsch & Maniatis, *Molecular Cloning: A Laboratory Manuial,* Second Edition (1989) Cold Spring Harbor Laboratory Press, Cold Spring Harbor, N.Y. [herein "Sambrook et al., 1989"]; *DNA Cloning: A Practical Approach,* Volumes I and II [D. N. Glover ed. 1985]; *Oligonucleotide Synthesis* [M. J. Gait ed. 1984]; *Nucleic Acid Hybridization* [B. D. Harnes & S. J. Higgins eds. (1985)]; *Transcription And Translation* ]B. D. Hames & S. J. Higgins, eds. (1984)]; *Animal Cell Culture* [R. I. Freshney, ed. (1986)]. *Immobilized Cells And Enzymes* [IRL Press, (1986)], B. Perbal, *A Practical Guide To Molecular Cloning* (1984): F. M. Ausubel et al. (eds.), *Current Protocols in Molecular Biology,* John Wiley & Sons, Inc. (1994)].

Peptides comprising at least two regions, each region comprising at least one T cell epitope of a antigen 5 are also within the scope of the invention. Each region of such peptides is derived from the same or from different antigen 5. Isolated peptides, each comprising at least two T cell epitopes of antigen 5, are particularly desirable for increased therapeutic effectiveness. Peptides immunologically related by T cell cross-reactivity, which are capable of reacting with the same T cells as a peptide of the invention, are also contemplated.

As noted above, isolated peptides of the invention can be produced by recombinant DNA techniques in a host cell transformed with a nucleic acid having a sequence encoding such peptide. The isolated peptides of the invention can also be produced by chemical synthesis. In certain limited situations, isolated peptides can be produced by chemical cleavage of the protein allergen. When a peptide is produced by recombinant techniques, host cells transformed with a nucleic acid having a sequence encoding the peptide or the functional equivalent of the nucleic acid sequence are cultured in a medium suitable for the cells and peptides can be purified from cell culture medium, host cells, or both using techniques known in the art for purifying peptides and proteins including ion-exchange chromatography, gel filtration chromatography, ultrafiltration, electrophoresis, or imrnunopurification with antibodies specific for the peptide, antigen 5 from which the peptide is derived, or a portion thereof. Isolated peptides of the invention are substantially free of cellular material or culture medium when produced by recombinant DNA techniques, or substantially free of chemical precursors or other chemicals when synthesized chemically.

Naturally, the present invention provides expression vectors and host cells transformed to express the peptides. A nucleic acid sequence coding for a peptide of the invention may be expressed in bacterial cells such as *E. coli,* insect cells (baculovirus), yeast, or mammalian cells such as Chinese hamster ovary cells (CHO). Suitable expression vectors, promoters, enhancers, and other expression control elements may be found in Sambrook et al. *Molecular Cloning: A Laboratory Manual,* second edition, Cold Spring Harbor Laboratory Press, Cold Spring Harbor, N.Y. (1989). Other suitable expression vectors, promoters, enhancers, and other expression elements are known to those skilled in the art. Many yeast and bacterial vectors are commercially available or on deposit at various depositories. Baculovirus and mammalian expression systems are also available.

For expression in *E. coli,* suitable expression vectors include, among others, pTRC [Amann et al., *Gene,* 69:301–315, (1988)], pGEX (Amrad Corp., Melbourne, Australia); pMAL (N.E. Biolabs. Beverly, Mass.); pRIT5 (Pharmacia, Piscataway, N.J.); pET-11d (Novagen, Madison, Wis.) [Jameel et al., *J. Virol.* 64:3963–3966 (1990)]: pQE12 (QIAGEN, Chatsworth, Calif.): and pSEM [Knapp et al., *BioTechniques,* 8:280–281 (1990)]. The use of pTRC, and pET-111d, for example, will lead to the expression of unfused protein. The use of pMAL, pRIT5, pSEM, pQE12, and pGEX will lead to the expression of allergen fused to maltose E binding protein (pMAL), protein A (pRIT5), truncated β-galactosidase (PSEM), hexahistidine (pQE12), or glutathione S-transferase (pGEX). When a polypeptide allergen is expressed as a fusion protein, it is particularly advantageous to introduce an enzymatic cleavage site at the fusion junction between the carrier protein and a polypeptide. The immnunodominant polypeptide (harboring the peptide of the invention) may then be recovered from the fusion protein through enzymatic cleavage at the enzymatic site and biochemical purification using conventional techniques for purification of proteins and peptides. Suitable enzymatic cleavage sites include those for blood clotting Factor Xa or thrombin for which the appropriate enzymes and protocols for cleavage are commercially available from, for example, Sigma Chemical Company, St. Louis, Mo. and N.E. Biolabs, Beverly, Mass. The different vectors also have different promoter regions allowing constitutive or inducible expression with, for example, IPTG induction (PRTC, Amann et al., (1988), supra; pET-11d. Novagen, Madison, Wis.) or temperature induction (pRIT5, Pharmacia, Piscataway, N.J.).

Human T cell stimulating activity can be tested by culturing T cells obtained form an individual sensitive to vespid venom (i.e., an individual who has an IgE mediated immune response to antigen 5) with an immunodominant peptide of the invention and determining whether proliferation of T cells occurs in response to the peptide as measured, e.g., by cellular uptake of tritiated thymidine. Stimulation indices for responses by T cells to peptides can be calculated as the maximum CPM in response to a peptide divided by the control CPM. A T cell stimulation index (S.I.) equal to or greater than two times the background level is considered "positive." Positive results are used to calculate the mean stimulation index for each peptide for the ;roup of peptides tested. Peptides of this invention comprise at least one T cell epitope and have a mean T cell stimulation index of greater than or equal to 2.0. Preferably the S.I. value is greater than four. A peptide having a T cell stimulation index of greater than or equal to 2.0, and more preferably greater than or equal to 4.0, is considered useful as a therapeutic agent. Preferred peptides have a mean T cell stimulation index of at least 2.5, more preferably at least 3.5, even more preferably at least 4.0, and most preferably at least 5.0.

In addition, preferred peptides have a positivity index (P.I.) of at least about 100, more preferably at least 150, even more preferably at least about 200 and most preferably at least about 250. The positivity index for a peptide is determined by multiplying the mean T cell stimulation index by the percent of individuals, in a population of individuals sensitive to vespid venom (e.g., preferably at least 9 individuals, more preferably at least 16 individuals or more, more preferably at least 29 individuals or more, or even more preferably at least 30 individuals or more), who have T cells that respond to the peptide. Thus, the positivity index represents both the strength of a T cell response to a peptide (S.I.) and the frequency of a T cell response to a peptide in a population of individuals sensitive to vespid venom.

In order to determine precise T cell epitopes by, for example, fine mapping techniques, a peptide having T cell stimulating activity and thus comprising at least one T cell epitope as determined by T cell biology techniques is modified by addition or deletion of amino acid residues at either the amino or carboxy terminus of the peptide and tested to determine a change in T cell reactivity to the modified peptide. If two or more peptides which share an area of overlap in the native protein sequence are found to have T cell stimulating activity, preferably human T cell stimulating activity, as determined by T cell biology techniques, additional peptides can be produced comprising all or a portion of such peptides and these additional peptides can be rested by a similar procedure. Following this technique, peptides are selected and produced recombinantly or synthetically. Peptides are selected based on various factors, including the strength of the T cell response to the peptide (e.g., stimulation index), the frequency of the T cell response to the peptide in a population of individuals sensitive to vespid venom, and the potential cross-reactivity of the peptide with other antigen 5 homologs. The physical and chemical properties of these selected peptides (e.g. solubility, stability) are examined to determine whether the peptides are suitable for use in therapeutic compositions or whether the peptides require modification as described herein. The ability of the selected peptides or selected modified peptides to stimulate human T cells (e.g., induce proliferation, lymphokine secretion) is determined.

Additionally, preferred peptides of the invention do not bind immunoglobulin E (IgE), or bind IgE to a substantially lesser extent than the protein allergen from which the peptide is derived binds IgE. The major complications of standard immunotherapy are IgE-mediate response such as anaphylaxis. Immunoglobulin E is a mediator of anaphylactic reactions which result from the binding and cross-linking of antigen to IgE on mast cells or basophils and the release of mediators (e.g., histamine, serotonin, eosinophil chemotactic factors). Thus, anaphylaxis in a substantial percentage of a population of individuals sensitive to vespid venom could be avoided by the use in immunotherapy of a peptide of peptides which do not bind IgE in a substantial percentage (e.g., at least about 75%) of a population of individuals sensitive to vespid venom allergen, or if the peptide binds IgE, such binding does not result in the release of mediators from mast cells or basophile. The risk of anaphylaxis could be reduced by the use in immunotherapy of a peptide or peptides which have reduced IgE binding. Thus, peptides which have minimal IgE stimulating activity, are desirable for therapeutic effectiveness. Minimal IgE stimulating activity refers to IgE production that is less than the amount of IgE production and/or IL-4 production stimulated by the native protein allergen.

A peptide of the invention. when administered to a vespid venom-sensitive individual. is capable of modify,ing the allergic response of the individual to the allergen. Particularly, peptides of the invention comprising at least one T cell epitope of antigen 5 when administered to an individual sensitive to vespid venom are capable of modifying T cell response of the individual to the allergen. As used herein, modification of the allergic response of an individual to vespid venom antigen 5 can be defined as non-responsiveness or diminution in symptoms upon exposure to antigen 5, as determined by standard clinical procedures [see e.g., Varney et al., *British Medical Journal*, 302:265–169 (1990)] including diminution in antigen 5 induced asthmatic symptoms. As referred to herein, a diminution in symptoms includes any reduction in allergic response of an individual to the allergen after the individual has completed a treatment regimen with a peptide or protein of the invention. This diminution may be subjective (i.e., the patient feels more comfortable in the presence of the allergen). Diminution in symptoms can be determined clinically as well, using standard skin tests as is known in the art.

As a result of the work described herein, peptides derived from antigen 5 comprising at least one T cell epitope can be produced. T cell epitopes are believed to be involved in initiation and perpetuation of the immune responses to allergen(s), which are responsible for the clinical symptoms of vespid venom. These T cell epitopes are thought to trigger early events at the level of the T helper cell by binding to an appropriate HLA (MHC) molecule on the surface of an antigen presenting cell and stimulating the relevant T cell subpopulation. These events lead to T cell proliferation, lymphokine secretion, local inflammatory reactions, the recruitment of additional immune cells to the site, and activation of the B cell cascade leading to production of antibodies. One isotype of these antibodies, IgE, is fundamentally important in the development of allergic symptoms and its production is influenced early in the cascade of events, at the level of the T helper cell, by the nature of the lymphokines secreted. A T cell epitope is the basic element or smallest unit of recognition by a T cell receptor where the epitope comprises amino acid residues essential to receptor recognition. Amino acid sequences which mimic those of T cell epitopes and which modify the allergic response to vespid venom antigen 5 are within the scope of this invention.

Exposure of vespid venom allergic patients to peptides of the present invention may tolerize or anergize appropriate T cell subpopulations such that they become unresponsive to vespid venom allergen(s), e.g., antigen 5, and do not participate in mounting an immune response upon such exposure. In addition, administration of a peptide of the present invention may modify the lymphokine secretion profile as compared with exposure to the naturally-occurring vespid venom allergin or portion thereof (e.g., result in a decrease of IL-4 and/or an increase in IL-2). Furthermore, exposure to a peptide of the invention may influence T cell subpopulations which normally participate in a response to vespid venom allergen(s) such that these T cells are drawn away from the site(s) of normal exposure to the allergen (e.g., nasal mucosa, skin, and lung) towards the site(s) of therapeutic administration of the peptide. This redistribution of T cell subpopulations may ameliorate or reduce the ability of an individual's immune system to mount an immune response at the site of normal exposure to the antigen 4, resulting in a diminution in allergic symptoms.

Isolated peptides of the invention comprise at least one T cell epitope of vespid venom antigen 5 and accordingly, the peptide comprises at least approximately eight amino acid residues of the protein allergen. For purposes of therapeutic effectiveness, therapeutic compositions of the invention preferably comprise at least two T cell epitopes of antigen 5. Accordingly, isolated peptides of the invention preferably comprise at least two T cell epitopes and accordingly, the peptide comprises at least approximately nine amino acid residues, and preferably at least 15 amino acid residues. Additionally, therapeutic compositions of the invention preferably comprise a sufficient percentage of the T cell epitopes of the entire protein allergen such that a therapeutic regimen of administration to the composition to an individual sensitive to vespid venom, results in T cells of the individual being tolerized to the protein allergen. Synthetically produced peptides of the invention comprising up to approximately 35 amino acid residues in length, and most preferably up to approximately 20 amino acid residues in length are particularly desirable as increases in length beyond this point may result in difficulty in peptide synthesis as well as retention of an undesirable property (e.g., immunoglobulin binding or enzymatic activity) due to maintenance of conformational similarity between the peptide and the protein allergen from which it is derived.

Another embodiment of the present invention provides peptides comprising at least two regions, each region comprising at least one T cell epitope of vespid venom antigen 5 and accordingly, each region comprises at least approximately seven amino acid residues. These peptides comprising at least two regions can comprise as many amino acid residues as desired and preferably comprise at least about 14, even more preferably about 25, and most preferably at most about 35 amino acid residues of antigen 5. Each region of such peptide preferably comprises up to 20 amino acid residues in length, more preferably up to 15 residues in length and most preferably up to 10 amino acid residues in length as increases in length of a region may result in difficulty in peptide synthesis as well as retention of an undesirable property (e.g., immunoglobulin binding or enzymatic activity) due to maintenance of conformational similarity between the peptide and the protein allergen from which it is derived. If desired, the amino acid sequences of the regions can be produced and joined by a linker to increase sensitivity to processing by antigen-presenting cells. Such linker can be any non-epitope amino acid sequence or other appropriate linking or joining agent. To obtain preferred peptides comprising at least two regions, each comprising at least one T cell epitope, the regions are arranged in a configuration different from a naturally-occurring configuration of the regions in the allergen or a combination of different antigen 5s. For example, the regions containing T cell epitope(s) can be arranged in a contiguous configuration and can preferably be derived from the same antigen or a combination of antigen 5 homologs from different species. Noncontiguous is defined as an arrangement of regions containing T cell epitope(s) which is different from that of an amino acid sequence present in the protein allergen from which the regions are derived. Furthermore, the noncontiguous regions containing T cell epitopes can be arranged in a nonsequenitial order (e.g., in an arrangement different from the order of the arrangement found in the native protein allergen from which the region containing T cell epitope(s) are derived).

The present invention further provides for modification or derivatization of peptides in a library. Modifications of peptides are well known to one of ordinary skill, and include phosphorylation, carboxymethylation, and acylation. Modifications may be effected by chemical or enzymatic means.

It is also possible to modify the structure of a peptide of the invention for such purposes as increasing solubility, enhancing therapeutic or preventive efficacy, or stability (e.g., shelf life ex vivo, and resistance to proteolytic degradation in vivo). A modified peptide can be produced in which the amino acid sequence has been altered, such as by amino acid substitution, deletion, or addition, to modify immunogenicity and/or reduce allergenicity, or to which a component has been added for the same purpose.

For example, a peptide can be modified so that it maintains the ability to induce T cell anergy and bind MHC proteins without the ability to induce a strong proliferative response or possibly, any proliferative response when administered in immunogenic form. In this instance, critical binding residues for the T cell receptor can be determined using known techniques (e.g., substitution of each residue and determination of the presence or absence of T cell reactivity). Those residues shown to be essential to interact with the T cell receptor can be modified by replacing the essential amino acid with another, preferably similar amino acid residue (a conservative substitution) whose presence is shown to enhance, diminish but not eliminate, or not affect T cell reactivity. In addition, those amino acid residues which are not essential for T cell receptor interaction can be modified by being replaced by another amino acid whose incorporation may enhance, diminish or not affect T cell reactivity, but does not eliminate binding to relevant MHC.

Additionally, peptides of the invention can be modified by replacing an amino acid shown to be essential to interact with the MHC protein complex with another, preferably similar amino acid residue (conservative substitution) whose presence is shown to enhance, diminish but not eliminate, or not effect T cell activity. In addition, amino acid residues which are not essential for interaction with the MHC protein complex but which still bind the MHC protein complex can be modified by being replaced by another amino acid whose incorporation may enhance, not effect, or diminish but not eliminate T cell reactivity. Preferred amino acid substitutions for non-essential amino acids include, but are not limited to, substitutions with alanine, glutamic acid, or a methyl amino acid.

Another example of a modification of peptides is substitution of cysteine residues preferably with serine, threonine, leucine or glutamic acid to minimize dimerization via disulfide linkages.

In order to enhance stability and/or reactivity, peptides can also be modified to incorporate one or more polymorphism in the amino acid sequence of a protein allergen resulting from natural allelic variation or from homologous peptides. Additionally, D-amino acids, non-natural amino acids, or non-amino acid analogs can be substituted or added to produce a modified peptide within the scope of this invention. Furthermore, peptides of the present invention can be modified using the polyethylene glycol (PEG) method of A. Sehon and co-workers (Wie et al., supra) to produce a peptide conjugated with PEG. In addition, PEG can be added during chemical synthesis of a peptide of the invention. Modifications of peptides or portions thereof can also include reduction/alkylation [Tarr in: *Methods of Protein Microcharacrerization*, J. E. Silver ed., Humana Press: Clifton, N.J. pp. 155–194) (1986)]; acylation [Tarr. supra], esterification [Tarr, supra], chemical coupling to an appropriate carrier [Mishell and Shiigi, eds., *Selected Methods in Cellular Immunology*, WH Freeman: San Francisco, Calif. (1980); U.S. Pat. No. 4,939,239]; or mild formalin treatment [Marsh, *Int. Arch. Allergy App. Immunol.*, 42:199–215 (1971)].

To facilitate purification and potentially increase solubility of peptides of the invention, it is possible to add reporter group(s) to the peptide backbone. For example, polyhistidine can be added to a peptide to purify the peptide on immobilized metal ion affinity chromatography [Hochuli, E. et al., *Bio/Technology* 6:1321–1325 (1988)]. In addition, specific endoprotease cleavage sites can be introduced, if desired, between a reporter group and amino acid sequences of a peptide to facilitate isolation of peptides free of irrelevant sequences. In order to successfully desensitize an individual to a protein antigen, it may be necessary to increase the solubility of a peptide by adding functional groups to the peptide or by not including hydrophobic T cell epitopes or regions containing hydrophobic epitopes in the peptides.

To potentially aid proper antigen processing of T cell epitopes within a peptide, canonical protease sensitive sites can be recombinantly or synthetically engineered between regions, each comprising at least one T cell epitope. For example, charged amino acid pairs, such as KK or RR, can be introduced between regions within a peptide during recombinant construction of the peptide. The resulting peptide can be rendered sensitive to cathepsin and/or other trypsin-like enzymes cleavage to generate portions of the peptide containing one or more T cell epitopes. In addition, such charged amino acid residues can result in an increase in solubility of a peptide.

Fatty acyl peptide derivatives may also be prepared. For example, and not by way of limitation, a free amino group (N-terminal or lysyl) may be acylated, e.g., myristoylated. In another embodiment an amino acid comprising an aliphatic side chain of the structure —$(CH_2)_n CH_3$ may be incorporated in peptides of the library. This and other peptide-fatty acid conjugates suitable for use in the present invention are disclosed in U.K. Patent GB-8809162.4, International Patent Application PCT/AU89/00166.

Activity Assays With Peptides of the Invention

Numerous assays are known in immunology for evaluating the immunomodulatory activity of an antigen. For example, the immunodominant vespid venom can be used in diagnostic assays for allergic diseases, which are described in detail, infra. In general, such peptides can be tested for the ability to induce proliferation of T cells from allergic subjects, without reacting with antibodies specific for antigen 5. Preferably, such antibodies that are not reactive with the peptides of the invention in the diagnostic assay are of the IgE class. It is important to note that natural allergen-specific antibodies have been found to bind weakly to denatured vespid venom allergens.

The peptides of the invention can be tested in a proliferation assay for T cell responses. Generally, lymphocytes from a sensitized host are obtained. The host can be a mouse that has been immunized with a vespid venom antigen 5, or with a crossreactive protein, such as testes specific protein. Using techniques that are well known in the art, T lymphocyte response to the peptide can be measured in vitro. In a specific embodiment, infra, T cell responses are detected by measuring incorporation of $^3$H-thymidine, which increases with DNA synthesis associated with proliferation. Cell proliferation can also be detected using an MTT assay [Mossman, *J. Immunol. Methods*, 65:55–63,(1983); Niks and Otto, *J. Immunol. Methods*, 130:140–151 (1990)]. Alternatively, lymphokine production assays can be practiced according to the present invention. In one embodiment, lymphokine production can be assayed using immunological or co-stimulation assays [see, e.g., Fehlner et al., *J. Immunol.*, 146:799 (1991)] or using the ELISPOT technique [Czerkinsky, et al., *J. Immunol. Methods*, 110:29 (1988)]. Alternatively, mRNA for lymphokines can be detected, e.g., by amplification [see Brenner, et al., *Biotechniques*, 7:1096 (1989)] or in situ hybridization [see, e.g., Kasaian and Biron, *J. Immunol.*, 142:1287 (1989)]. Of particular interest are those individuals whose T cells produce lymphokines associated with IgE isotype switch events, e.g., IL-4 and IL-5 [Purkeson and Isakson, *J. Exp. Med.*, 175:973–982 (1992)]. Also of interest are the peptide fragments of the vespid venom antigen 5 that contain epitopes recognized by T cells involved in IgE switch events. Any method for detecting T cell proliferation known in the art can be used with the immunodominant vespid antigen 5 peptides obtained according to the present invention.

Thus, in a preferred aspect, the peptides of the present invention can be used in in vitro assays with peripheral blood lymphocytes or cell lines derived from peripheral blood lymphocytes, obtained from vespid venom antigen 5 sensitive individuals to detect secretion of lymphokines ordinarily associated with allergic responses, e.g., IL-4. Such assays may indicate which epitopes are responsible or associated with the allergic condition. In this way, specific epitopes responsible for T cell responses associated with allergic response can be identified. The sequences of such epitopes can be compared to other vespid venom antigen 5s and to environmental or autologous proteins to determine if there are sequence similarities that suggest possible cross-reactivity. The peptides can be tested for the ability to induce T cell anergy, e.g., by mega-dose administration, modification to produce an epitope antagonist, administration in the absence of the appropriate costimulatory signals, and other methods thought to result in T cell anergy. Peptides containing such epitopes are ideal candidates for therapeutics.

In a further embodiment, the polypeptides of the invention can be used directly in assays to detect the extent of cross-reactivity with other environmental proteins and/or homologous proteins, with which they share sequence similarity. In particular, the immunodominant fragments of the vespid venom antigen 5s that have sequence similarity with such environmental, and more particularly, homologous proteins can be evaluated for cross reactivity with antibodies or T cell specific for such proteins. In a specific embodiment, the cross reactivity of vespid venom antigen 5s with human and mouse testes specific protein can be evaluated.

Diagnostic and Therapeutic Uses of the Peptides

The present invention identifies therapeutically relevant polypeptide fragment of vespid venom antigen 5. The invention contemplates use of the imnunoactive fragments of vespid venom antigen 5 for the preparation of diagnostic or therapeutic compositions, for the use in the diagnosis and therapy of vespid venom allergen-specific allergic conditions. In particular, vespid antigen 5 from *Dolichovespula maculata* (white-face hornet) (Dol m V), *Dolichovespula arenaria* (yellow hornet) (Dol a V), *Vespula vulgaris* (yellowjacket) (Ves v V), *Vespula maculifrons* (yellowjacket) (Ves m V), *Polistes annularis* (wasp) (Pol a V), and *Polistes exclamans* (wasp) (Pol e V) are contemplated for use in diagnosis and therapy according to the present invention. Other vespid species known to harbor antigen 5, and thus represent additional antigen 5 species of the invention, include but are not limited to *Vespa crabo* (European hornet), *V. flavopilosa* (yellow jacket), *V. germanica* (yellowjacket), *V. pennsylvannica* (yellowjacket), *V. squamosa* (yellowjacket), *V. vidue* (yellowjacket), and *P. fuscatus* (paperwasp).

Diagnostic Methods

The present invention contemplates in vitro diagnostic assays on peripheral blood lymphocytes, as described supra. Such diagnostic assays can give detailed information about the antigen 5-specific T cell responses, the phenotype of the T cell response, and preferably the T cell epitope of the antigen 5 involved in T cell responses. The inimunodominant epitope and the epitope involved in IgE isotype class switch events can be detected, if they are not the same. In particular, the T cell epitopes of vespid venom antigen 5s that stimulate proliferation and/or lymphokine secretion of T cells of a phenotype associated with IgE isotype class switching events can be identified for a specific individual, or for a class of individuals who share MHC haplotype or a predominant T cell receptor variable region expression, or both.

In vivo assays for allergenicity generally consist of skin prick sensitivity assays, in which serially diluted amounts of an allergen are administered either subcutaneously or intradermally into a patient's skin, and wheel and erythema reactions are detected. As with in vitro assays, the availability of pure venom antigen 5 peptides greatly increases the value of the results of the in vivo diagnostic assays since cross-reactivity with impurities in extracts prepared from vespid venom sacs, and uncertainty about the epitope specificity can be avoided.

Therapeutic Methods

Therapeutic compositions of the invention (see, infra) can be used in immunotherapy, also referred to as hyposensitization therapy. Immunotherapy has proven effective in allergic diseases, particular insect allergy. Allergens are administered parenterally over a long period of time in gradually increasing doses. Such therapy may be particularly effective when the allergen or allergens to which the patient is sensitive have been specifically identified and the therapy is targeted to those allergen(s). Thus, the availability of specific, pure vespid venom antigen 5 peptide(s) in large quantities is important for immunotherapy of allergy.

The present invention contemplates use of peptides containing at least an immunomodulatory T cell epitope of a vespid venom antigen 5 to induce specific T cell anergy to the vespid venom antigen 5. Such immunomodulatory peptide contains one or more immunodominant epitope of antigen 5. A peptide comprising such a T cell epitope and lacking a B cell epitope can be administered to a patient. As discussed supra, the presence of B cell epitopes on an allergen can cause an undesirable systemic reaction when the allergen is used for immunotherapy. Thus, a particular advantage of the invention is the capability to provide allergen polypeptides that do not cause undesirable systemic effects.

In one embodiment, one or more peptides can be injected subcutaneously to decrease the T cell response to the entire molecule, e.g., as described by Briner et al. [*Proc. Natl. Acad. Sci. U.S.A.*, 90:7608–12 (1993)]. In another embodiment, one or more peptide can be administered intranasally to suppress allergen-specific responses in naive and sensitized subjects [see e.g., Hoyne et al., *J. Exp. Med.*, 178:1783–88 (1993)].

Administration of a vespid venom antigen peptide of the invention is expected to induce anergy, resulting in cessation of allergen-specific antibody production or allergen-specific T cell response, or both, and thus, have a therapeutic effect.

In a preferred aspect of the invention, peptide-based therapy to induce T cell anergy is customized for each individual or a group of individuals. Using the diagnostic methods of the present invention, the specific T cell epitope or epitopes of a vespid venom antigen 5 involved in the allergic response can be identified. Peptides comprising these epitopes can then be used in an individualized immunotherapy regimen.

For example, by analogy and based on the data shown in Table 4, infra, a treatment protocol for BALB/c mice could include peptides 1, 5, 6, 11, 15, 20, and 18, while treatment of ASW/Sn mice might include peptides 6, 7, and 18: treatment of C3H/He might include peptides 2, 5, and 15, and treatment of P/J mice might include peptides 1, 9, and 15.

Administration of the therapeutic compositions of the present invention to desensitize an individual can be carried out using known techniques. For example, one or more immunodominant peptides of the invention comprising at least one T cell epitope can be administered in combination with an appropriate diluent, a carrier, and/or an adjuvant. To induce T cell anergy in an individual, the therapeutic composition is preferably administered in non-immunogenic form, e.g., it does not contain adjuvant. Pharmaceutically acceptable diluents include saline and aqueous buffer solutions. Pharmaceutically acceptable carriers include polyethylene glycol [Wie et al., *International Archives of Allergy and Applied Immunology*, 64:84–99 (1981)] and liposomes [Strejan et al., *Journal of Neuroimmunology*, 7:27 (1984)]. Such compositions will generally be administered by injection (subcutaneous, intravenous, etc.), oral administration (e.g., as in the form of a capsule), transdermal application, or transmucosal administration (e.g. nasal, buccal, or rectal administration). The therapeutic compositions of the invention are administered to individuals sensitive to vespid venom at dosages and for lengths of time effective to reduce sensitivity (i.e., reduce the allergic response) of the individual to vespid stings. A therapeutically effective amount of one or more of the same or different therapeutic compositions can be administered simultaneously or sequentially to an individual sensitive to vespid venom. Effective amounts of the therapeutic compositions will vary according to factors such as the degree of sensitivity of the individual to vespid venom, the age, sex, and weight of the individual, and the ability of the peptide to stimulate a T cell response in the individual.

In yet another aspect of the present invention, a composition is provided comprising at least two immunodominant peptides (e.g., a physical mixture of at least two peptides), each comprising at least one T cell epitope of antigen 5. The peptides are derived from the same or from different homologs of antigen 5. Such compositions can be administered in the form a therapeutic composition with a pharmaceutically acceptable carrier of diluent. A therapeutically effective amount of one or more of such compositions can be administered simultaneously or sequentially to an individual sensitive to vespid venom.

Transmucosal administration. According to the invention, any transmucosal route of administration, including but not limited to rectal, oral, vaginal, buccal, etc. can be employed. In particular, the present invention is directed to the following transmucosal routes of administration. It can be readily appreciated that any of the transmucosal routes of administration may be enhanced by use of a mucosal penetration enhancer. The term "mucosal penetration enhancer" refers to a reagent that increases the rate or facility of transmucosal penetration of peptide, such as but not limited to, a bile salt, fatty acid, surfactant or alcohol. In specific embodiments, the permeation enhancer can be sodium cholate, sodium dodecyl sulphate, sodium deoxycholate, taurodeoxycholate, sodium glycocholate, dimethylsulfoxide or ethanol. Suitable penetration enhancers also include glycyrrhetinic acid (U.S. Pat. No. 5,112,804 to Kowarski) and polysorbate-80, the latter preferably in combination with an non-ionic surfactant such as nonoxynol-9, laureth-9, poloxamer-124, octoxynol-9, or lauramide-DEA (European Patent EP 0 242 643 B1 by Stoltz). The selection of a particular mucosal penetration enhancer may depend on the characteristics of the specific mucosa. These factors are addressed in greater detail below.

Administration Via Suppositories. In another aspect, peptide is formulated in a matrix suitable for rectal (or vaginal) insertion, i.e., in a suppository. The invention is not limited to any particular suppository formulation. Indeed, many suppository formulations are known in the art, e.g., as described in *Remington's Pharmaceutical Sciences, Physician's Desk Reference,* and *U.S. Pharmacopeia.*

Administration Via a Buccal Patch. According to the invention, peptide can be formulated in a buccal patch for administration via the interior of the cheek. It may be appreciated that a buccal patch constitutes another form of transmucosal administration. The technology for preparing buccal patch formulations is known in the art, e.g., *Remington's Pharmaceutical Sciences,* supra.

Oral-Pharyngeal Administration. In yet another embodiment, peptide can be formulated for oral-pharyngeal, including sublingual and transbuccal, administration. For example, peptide can be incorporated in a "candy" matrix, such as that described in U.S. Pat. No. 4,671,953, in a gum base, or a lozenge. In another embodiment, the peptide can be formulated in a capsule or pill form for sublingual placement. It is particularly contemplated that peptide for oral-pharyngeal administration may be formulated with a flavor masking agent or coating. Many flavor masking agents for use with oral pharmaceuticals are known in the art, and can be selected for use with the present invention.

Oral Administration. In still a further embodiment, peptide can be formulated for oral administration via the stomach and intestinal mucosa. For oral administration, peptide can be administered in a carrier designed for drug release in either the stomach (an acidic environment), or the intestines, or both. Many capsules, pills, and matrices for oral administration of a drug are known in the art, and can be selected on the basis of compatibility with peptide, and the desired point and rate of drug release by the ordinary skilled physician. Oral administration of peptide may require higher dosages than other routes of administration to overcome the effects of first pass metabolism by the liver.

Transdermal Administration. In a further embodiment, as noted above, the present invention is directed to cransdermal administration of peptide. Various and numerous methods are known in the art for transdermal administration of a compound, e.g., via a transdermal patch. These methods and associated devices provide for control of the rate and quantity of administration of a drug, and some allow for continuous modulation of drug delivery. Transdermal patches are described in, for example, U.S. Pat. No. 5,407,713, issued Apr. 18, 1995 to Rolando et al.; U.S. Pat. No. 5,352,456, issued Oct. 4, 1004 to Fallon et al.; U.S. Pat. No. 5,332,213 issued Aug. 9, 1994 to D'Angelo et al.; U.S. Pat. No. 5,336,168, issued Aug. 9, 1994 to Sibalis; U.S. Pat. No. 5,290,561, issued Mar. 1, 1994 to Farhadieh et al.; U.S. Pat. No. 5,254,346, issued Oct. 19, 1993 to Tucker et al.; U.S. Pat. No. 5,164,189, issued Nov. 17, 1992 to Berger et al.; U.S. Pat. No. 5,163,899, issued Nov. 17, 1992 to Sibalis; U.S. Pat. Nos. 5,088,977 and 5,087,240, both issued Feb. 18, 1992 to Sibalis; U.S. Pat. No. 5,008,110, issued Apr. 16, 1991 to Benecke et al.; and U.S. Pat. No. 4,921,475, issued May 1, 1990 to Sibalis, the disclosure of each of which is incorporated herein bv reference in its entirety.

It can be readily appreciated that a transdermal route of administration may be enhanced by use of a dermal penetration enhancer, e.g., such as enhancers described in U.S. Pat. No. 5,164,189 (supra), U.S. Pat. No. 5,008,110 (supra), and U.S. Pat. No. 4,879,119, issued Nov. 7, 1989 to Aruga et al., the disclosure of each of which is incorporated herein by reference in its entirety.

Pharmaceutically Acceptable Compositions

The in vivo diagnostic or therapeutic compositions of the invention may also contain appropriate pharmaceutically acceptable carriers, excipients, diluents and adjuvants. As used herein, the term "pharmaceutically acceptable" preferably means approved by a regulatory agency of a government, in particular the Federal government or a state government, or listed in the U.S. Pharmacopeia or another generally recognized pharmacopeia for use in animals, and more particularly in humans, although a pharmaceutically acceptable carrier may share the attributes of such approved or recognized carriers without having itself been approved or recognized. Examples of suitable pharmaceutical carriers are provided in "Remington's Pharmaceutical Sciences" by E. W. Martin.

Such pharmaceutically acceptable carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include mannitol, human serum albumin (HSA), starch, glucose, lactose, sucrose, gelatin, malt, rice, flour, chalk, silica gel, magnesium carbonate, magnesium stearate, sodium stearate, glycerol monostearate, talc, sodium chloride, dried skim milk, glycerol, propylene, glycol, water, ethanol and the like. These compositions can take the form of solutions, suspensions, tablets, pills, capsules, powders, sustained-release formulations and the like.

Such compositions will contain an effective diagnostic or therapeutic amount of the active compound together with a suitable amount of carrier so as to provide the form for proper administration to the patient. While intravenous injection is a very effective form of administration, other modes can be employed, such as by injection, or by oral, nasal, or parenteral administration.

The invention will be further clarified by the following examples, which are intended to be purely exemplary of the invention.

EXAMPLE 1

Mapping T Cell Epitopes of Dol M Ag5

In the present Example, a series of 15 to 20-residue peptides with 10-residue overlaps to encompass the entire white faced hornet Ag5 molecule (form 2) was synthesized. The sequences of these peptides are given in FIG. 2. These peptides were used for mapping T cell epitopes of hornet Ag5 by their stimulation of specific murine spleen cells immunized with native or recombinant Antigen 5. These peptides were also used to study the cross reacting T cell epitopes of hornet antigen 5 and a mouse testis protein Tpx [Mizuku et al., *Mammalian Genome*, 3:274–280 (1992)]. This cross reactivity is suggested by the partial sequence identity of hornet antigen 5 with mouse and human testis proteins (FIG. 3).

Results

Antibody response in mice of different haplotypes to recombinant hornet Ag5. Five strains of mice were immunized with recombinant (r) white faced hornet Ag5 and alum as adjuvant. Four strains were found to be high antibody responders for r-white faced hornet Ag5: BALB/v byj, ASW/Sn, C3H/He, and P/J. Antibody responses were evaluated by direct ELISA [King et al., *J. Immunol.*, 154:577 (1995)]. The antibody titers (the reciprocal of the dilution yielding 50% of maximum signal extrapolated from ELISA curves in wells coated with r-Dol m 5.02 or n-Dol m 5.01) of these sera for n-(natural) and r-Ag5 are given in Table 3. One strain, C57B1/6, was found to be a poor antibody responder.

TABLE 3

Antibody for Mice of Different Strains Immunized with Recombinant White faced hornet Ag5

| Mice | | Half maximal Ab titer* | |
|---|---|---|---|
| Strain | Haplotype | r-Dol m 5.02 | n-Dol m 5.01 |
| C57B1/6 | b | $1 \times 10^2$ | $2 \times 10^1$ |
| BALB/c byj | d | $8 \times 10^4$ | $4 \times 10^4$ |
| C3H/He | k | $6 \times 10^3$ | $2 \times 10^3$ |
| P/J | p | $2 \times 10^4$ | $1 \times 10^4$ |
| ASW/Sn | s | $1 \times 10^5$ | $1 \times 10^5$ |

*Sera are from week five bleeding after three intraperitoneal immunizations with 0.2 ml of 10 µg/ml r-Dol m 5.02 and alum (5 µg/ml) in 0.05 m sodium phosphate buffer, pH 6.2, on weeks 0, 2, and 4.

Figure 5:
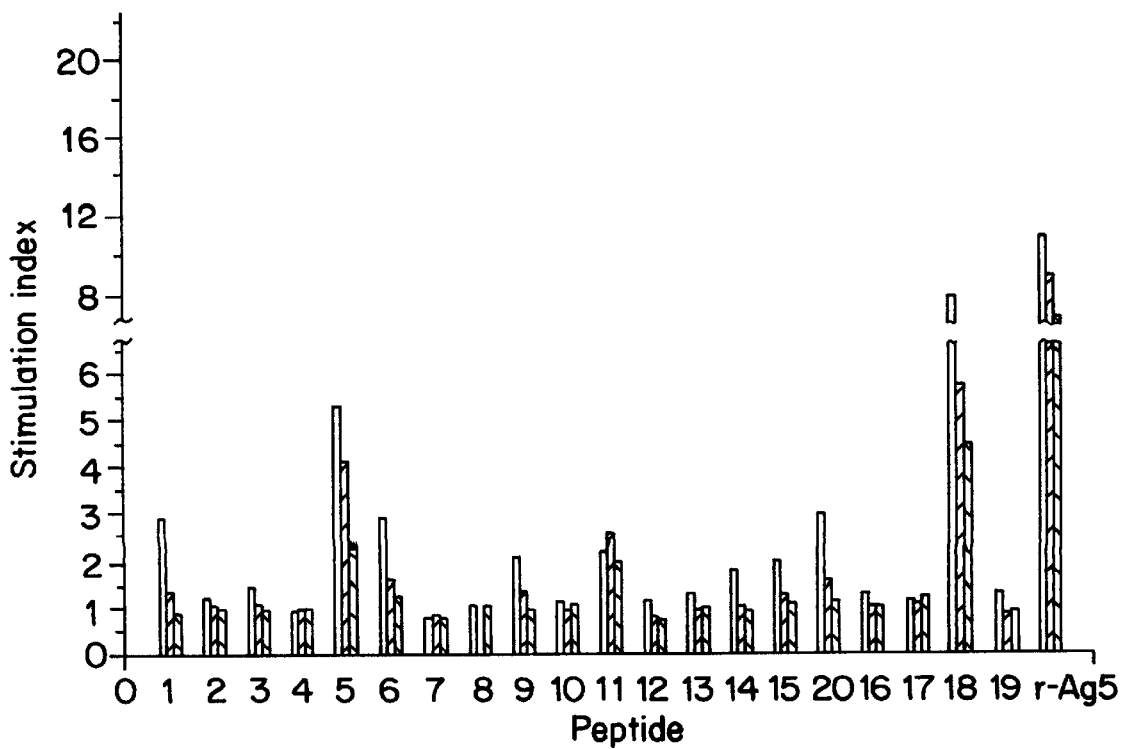
Figure 6:
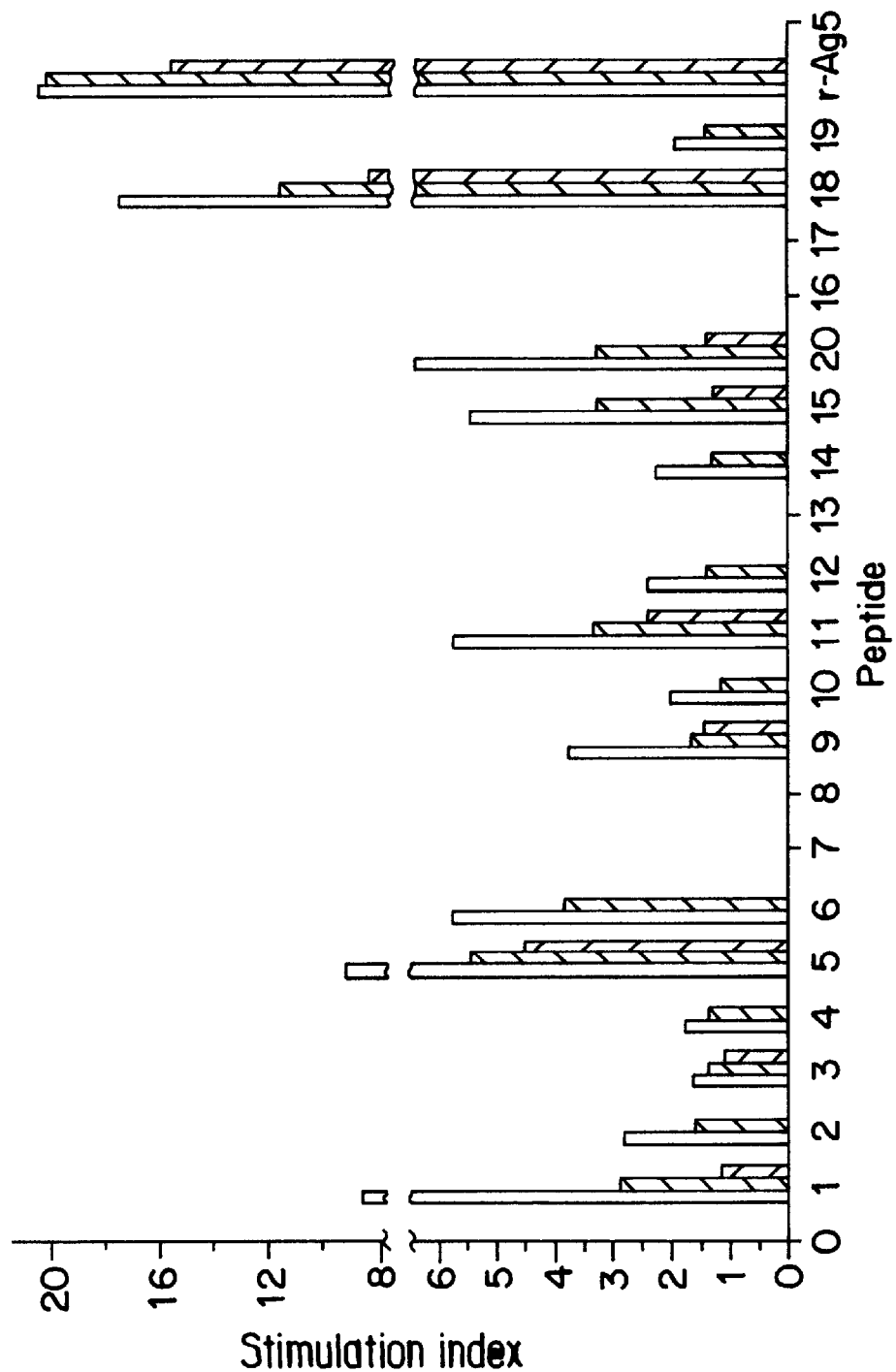

T cell response in BALB/c mice to natural hornet Ag5 and its recombinant protein or fragments. FIGS. 4 and 5 show the proliferative responses of spleen cells from BALB/c mice immunized 4 times with n- and r-Ag5 respectively. Nearly identical results show that r-Ag5 and n-Ag5 share common continuous T cell epitopes. Previous studies have shown that r-Ag5 lacks the discontinuous B cell epitopes of n-Ag5, as r-Ag5 is not properly folded with the disulfide bonds of n-Ag5 [King et al., *J. Immunol.*, 154:577–584 (1995)]. FIG. 6 shows the response of spleen cells from BALB/c mice immunized 5 times with r-Ag5. Higher proliferative responses were observed than those in FIG. 5, where mice were immunized 4 times with r-Ag5. The results in FIG. 4–6 together indicate that peptides 1, 5, 6, 11, 15, 20, and 18 contain the T cell epitopes of Ag5, if we assume that peptides have stimulation indices of ≧4 represent positive responses with a high degree of certainty.

Figure 7:
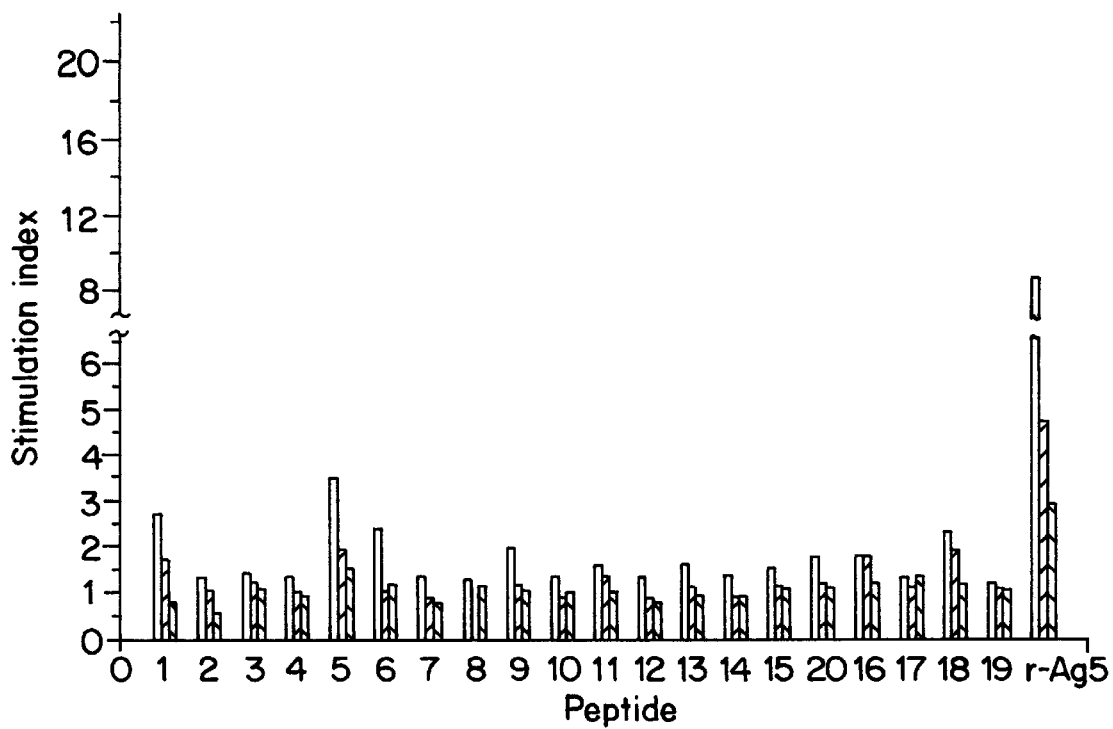
Figure 8:
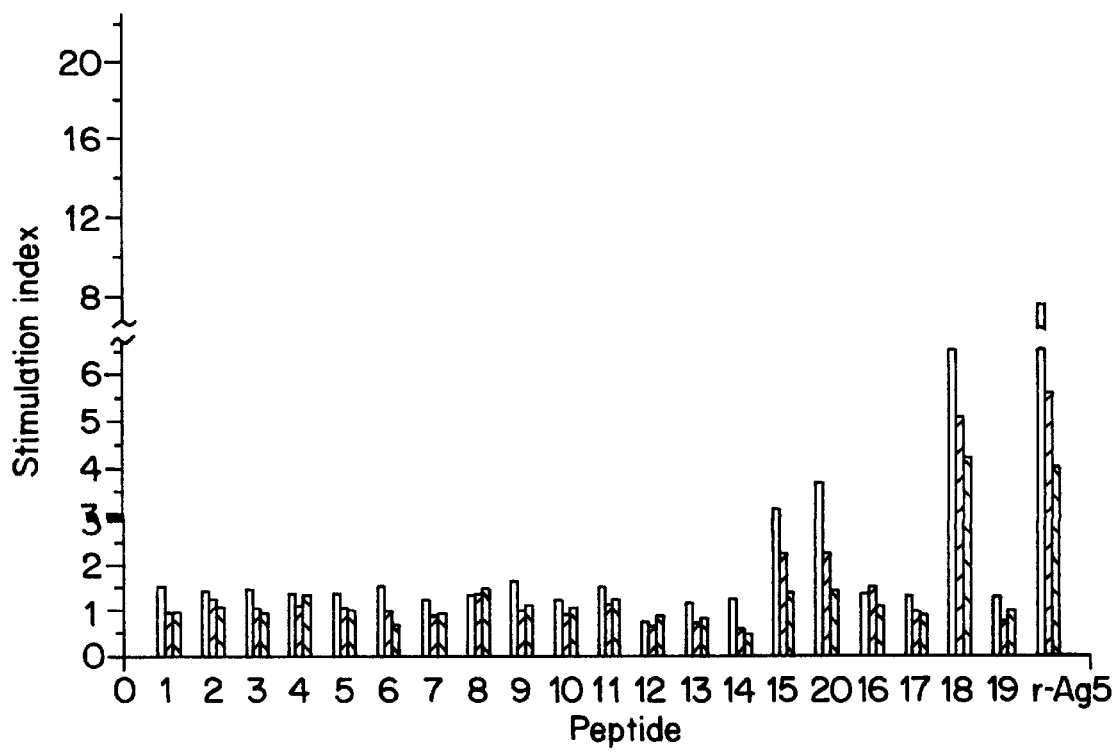
Figure 9:
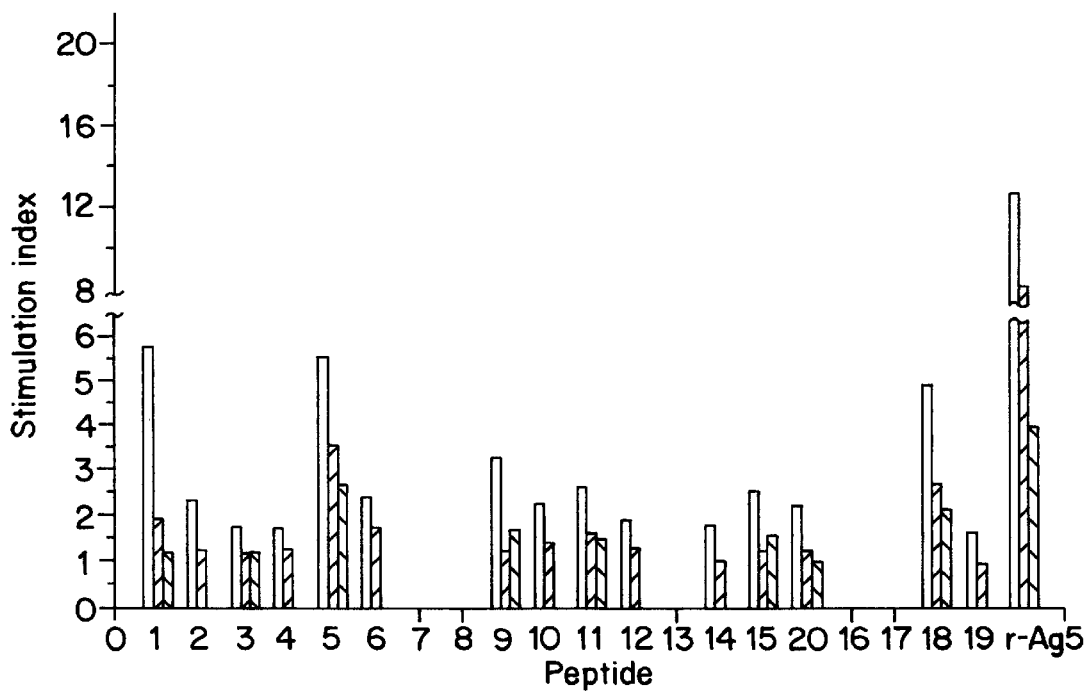
Figure 10:
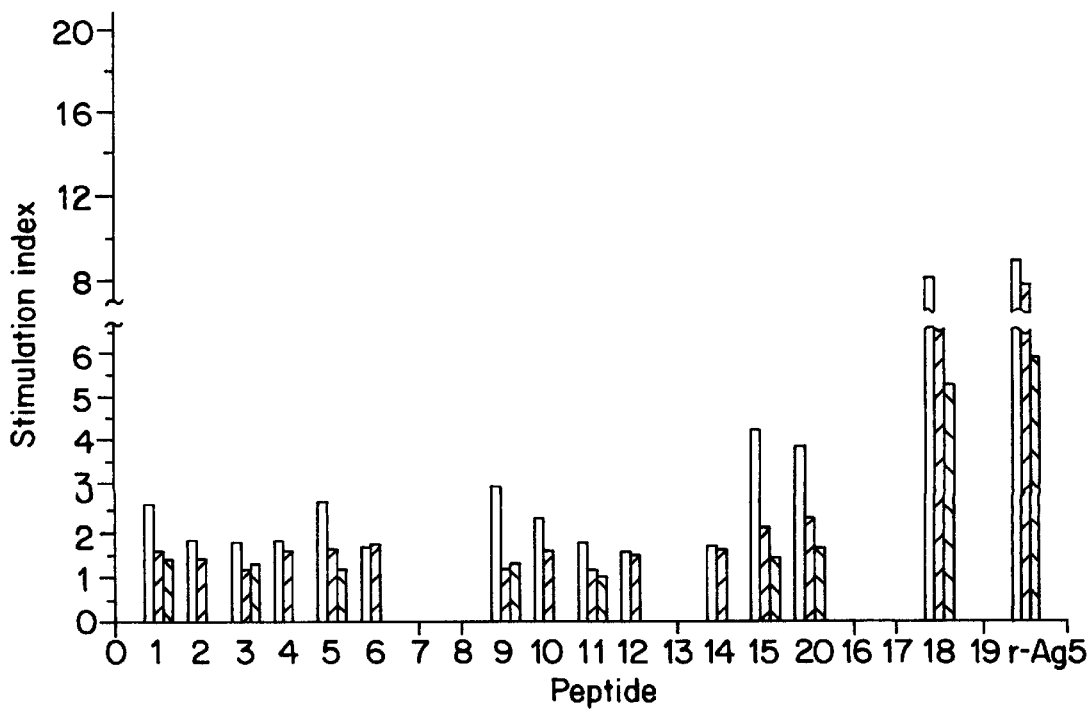

FIGS. 7 and 8 show the proliferation data with spleen cells from mice immunized 4 times with recombinant N-terminal and C-terminal fragments of antigen 5, labelled IN (residue 1-114) and C (residue 151-204), respectively. Similar but higher proliferation results were obtained with mice after 5 times immunization, as given in FIGS. 9 and 10. As to be expected, spleen cells from r-fragment IN or C immunized mice were stimulated by peptides whose sequences are represented by the immunogen. There is one exception shown in FIG. 9: spleen cells from r-fragment IN (residue 1-114) immunized mice were stimulated by peptide 18 (residue 176-195).

Figure 11:
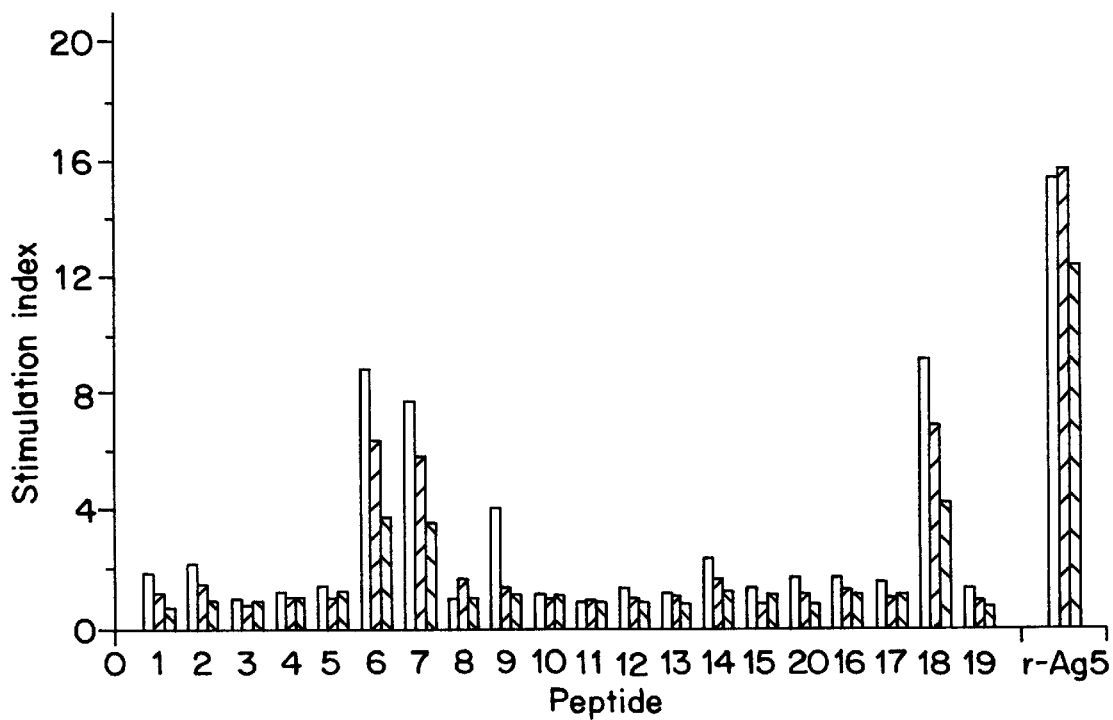
Figure 12:
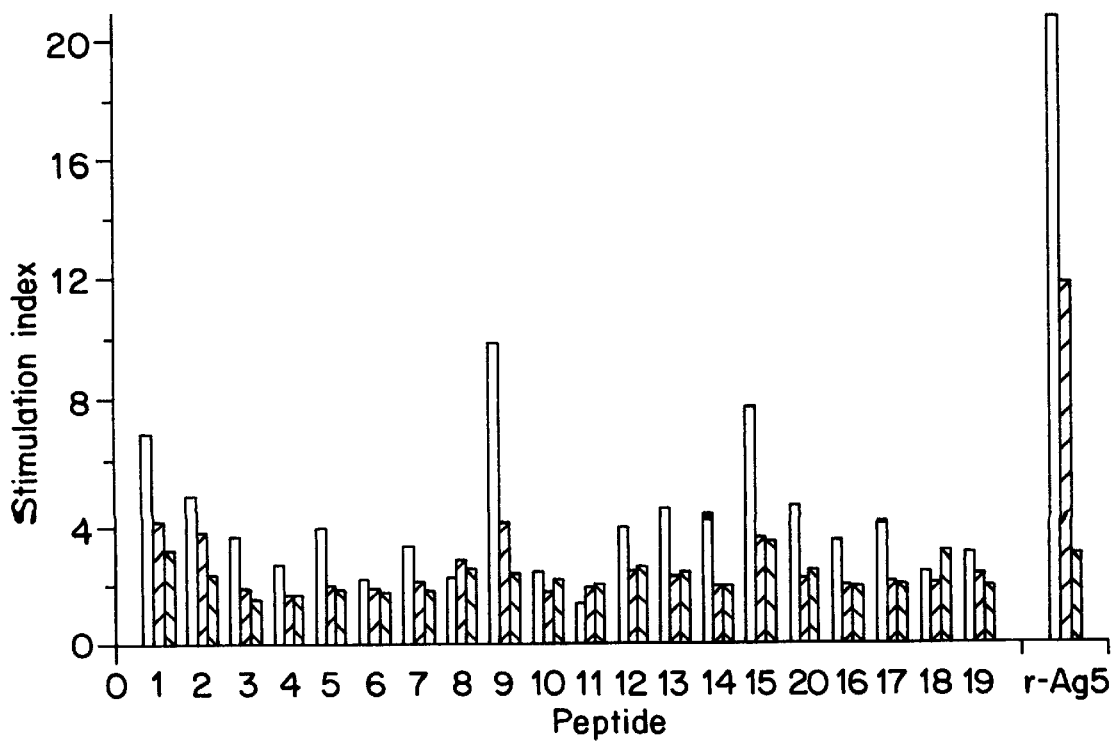
Figure 13:
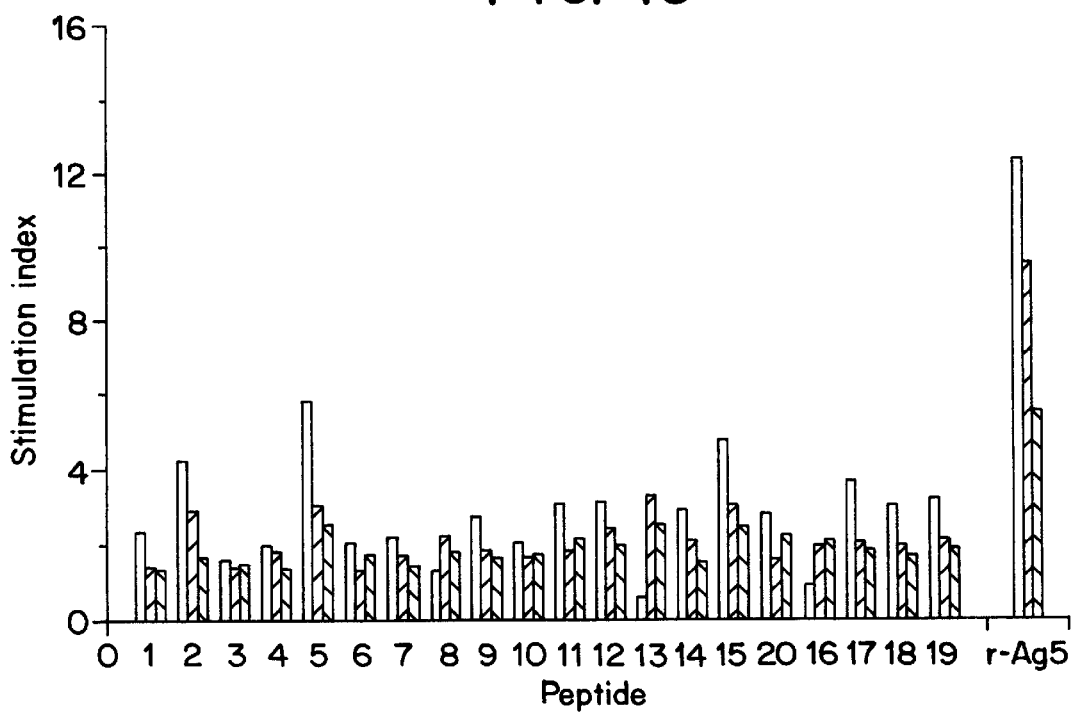

T cell response in mice of different haplotypes to recombinant hornet Ag5. FIGS. 11 to 13 show the proliferative response of spleen cells for mice of ASW/Sn, P/J, and C3H/He, respectively. The results for ASW/Sn mice in FIG. 11 indicate that there are four peptides with stimulation indices of ≧4: peptides 6, 7, 9, and 18. The results for P/J mice in FIG. 12 show multiple peptides with stimulation indices of ≧4: peptides 1, 2, 5, 9, 12, 13, 14, 15, 20, and 17. The data for C3H/He mice in FIG. 12 indicate three peptides with stimulation indices of ≧4: peptides 2, 5 and 15.

Figure 14:
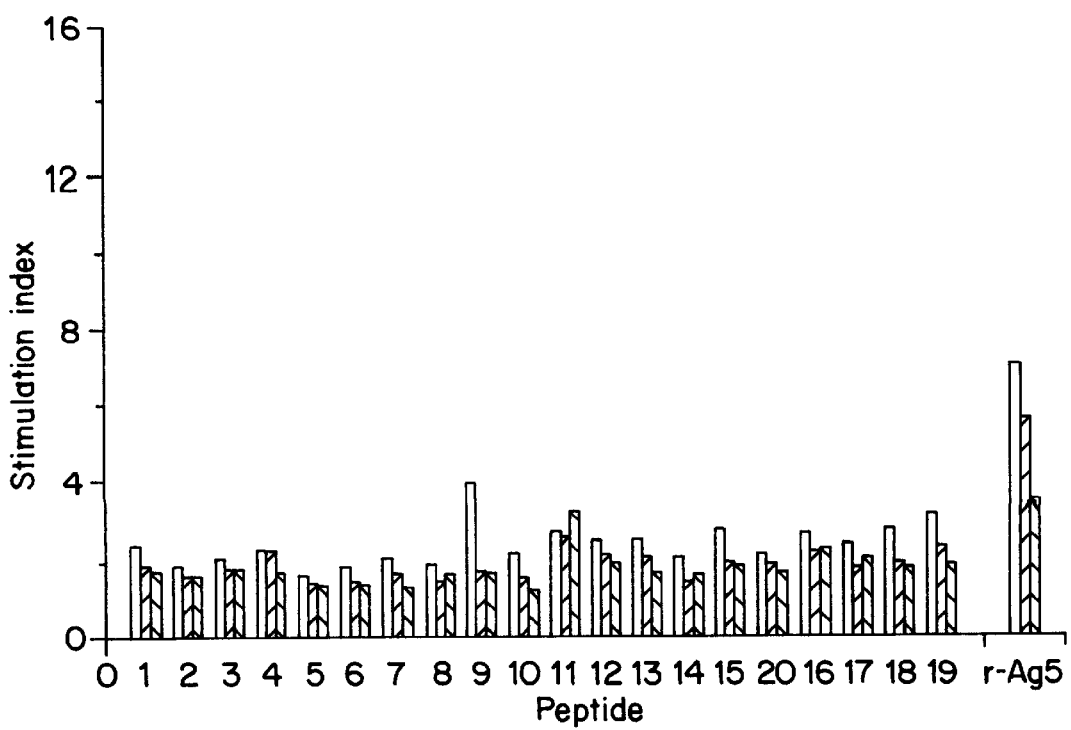

FIG. 14 shows the proliferation responses of spleen cells for C57B1/6 mice. Several peptides had stimulation indices of ≧2, but only one peptide, number 9, showed a stimulation index approaching 4. A lower proliferation response compared to the other mouse strains was also observed with r-Ag5 as a control. These data indicate that C57B/6 mice showed poor T cell responses to white faced hornet Ag5. as contrasted to the other 4 strains of mice tested (Table 4).

TABLE 4

Summary of proliferation indices of r-Ag5 specific spleen cells from mice of different strains on stimulation with the dominant T cell epitope peptides[1]

| Stimulating[2] antigen | Stimulation Index[3] | | | | |
|---|---|---|---|---|---|
| | BALB/c | ASW/Sn | C3H/He | P/J | C57B1/6 |
| Peptide 1 | 8.6 | 1.9 | 2.4 | 6.9 | 2.5 |
| 2 | 2.9 | 2.2 | 4.3 | 4.8 | 1.9 |
| 5 | 9.3 | 1.4 | 5.8 | 4.0 | 1.7 |
| 6 | 5.8 | 8.8 | 2.0 | 2.2 | 1.9 |
| 7 | (0.9) | 7.7 | 2.2 | 3.3 | 2.1 |
| 9 | 3.8 | 4.0 | 2.7 | 9.9 | 3.9 |
| 11 | 5.8 | 0.9 | 3.0 | 1.4 | 2.7 |
| 12 | 2.5 | 1.4 | 3.3 | 4.0 | 2.5 |
| 13 | (1.3) | 1.2 | 3.6 | 4.5 | 2.5 |
| 14 | 2.3 | 2.3 | 2.9 | 4.2 | 2.0 |
| 15 | 5.6 | 1.4 | 4.7 | 7.8 | 2.8 |
| 20 | 6.5 | 1.7 | 2.8 | 4.5 | 2.1 |
| 17 | (1.1) | 1.6 | 3.6 | 4.1 | 2.4 |
| 18 | 17.7 | 9.1 | 2.9 | 2.5 | 2.7 |
| r-Ag5 | 20.9 | 15.4 | 12.3 | 20.8 | 7.0 |
| Blank | 3970 cpm | 5640 cpm | 3130 cpm | 1730 cpm | 1050 cpm |

NOTES
[1]Dominant T cell epitopes are defined as those peptides which showed stimulation indices of ≧4 in at least one of 5 strains of mice tested.
[2]Peptides in bold face represent those with stimulation indices of ≧4 in 2 or more strains of mice.
[3]Stimulation index values are taken from FIGS. 5, 9, 10, 11 and 12, in which spleen cells were from mice immunized 5 times with r-Ag5. The exceptions are those values in parentheses which are taken from FIG. 4 in which spleen cells were from 4 times r-Ag5 immunized mice.

Figure 15:
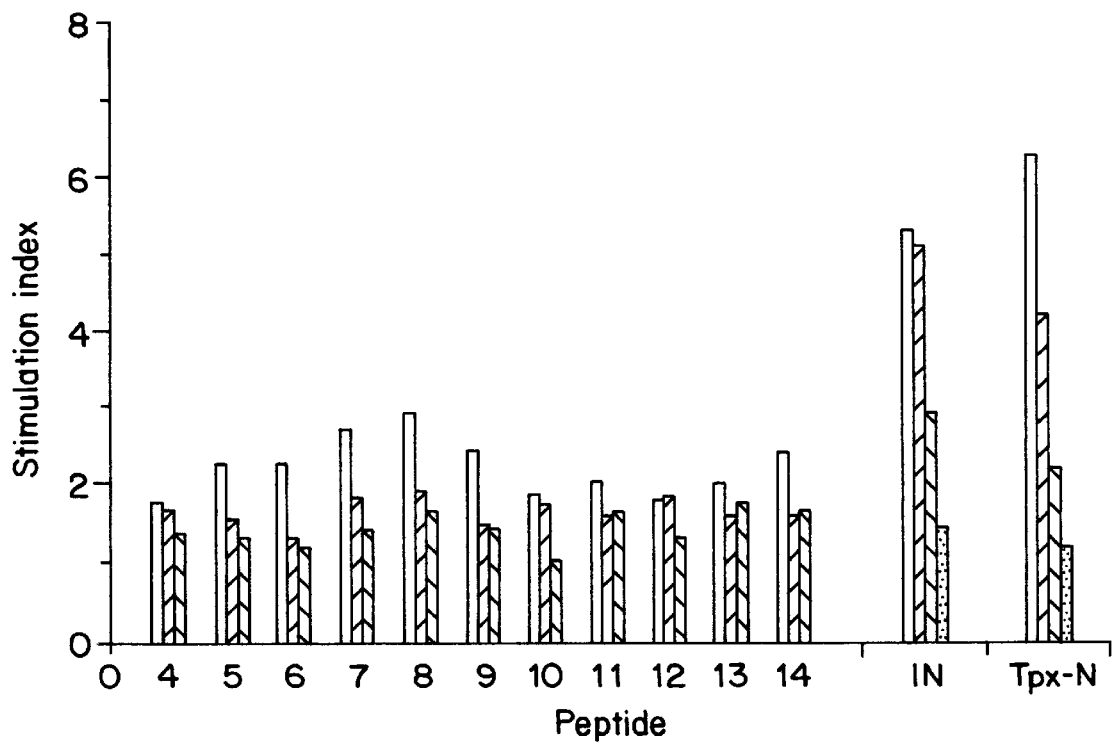
Figure 16:
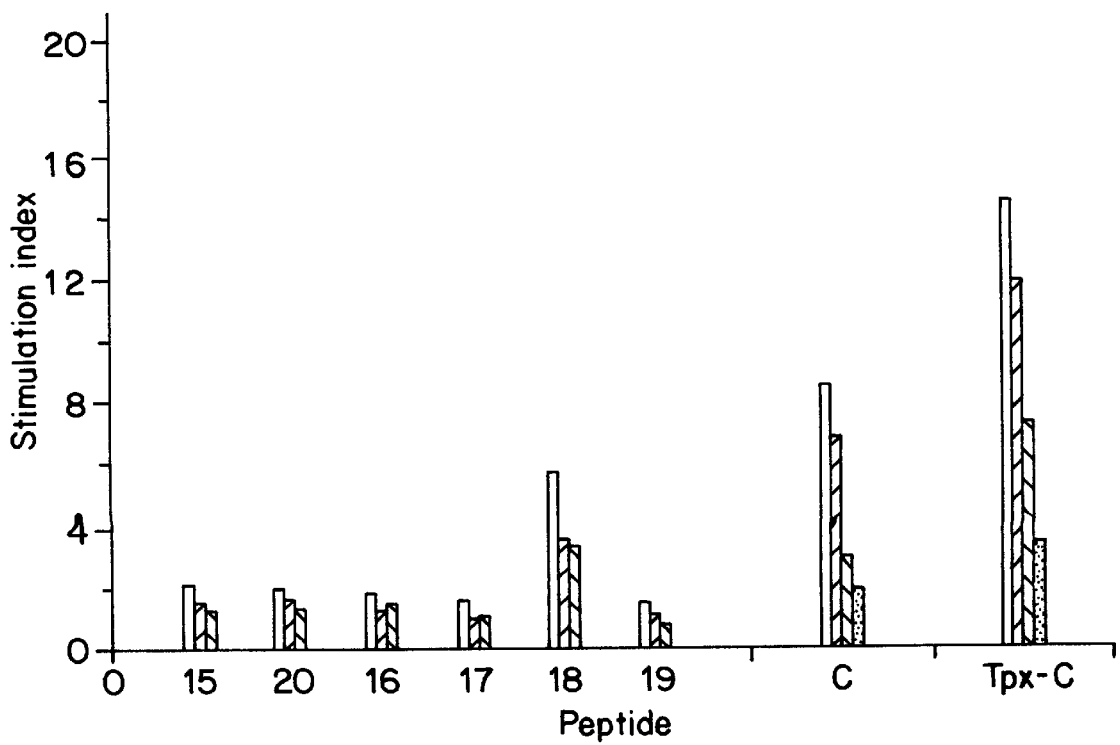

T cell epitopes of hornet Ag5 and a mouse testis protein Tpx. Cross reactivity of these two proteins was studied in mice immunized with their fragments (FIGS. 15 and 16). Spleen cells from BALB/c mice inmnunized with r-fragment Tpx-N (residue 14-106) responded equally well to stimulation with the immunogen or the r-fragment IN of hornet Ag5 (residue 1-114). Similarly spleen cells from BALB/c mice immunized with r-fragment Tpx-C (residue 101-163) responded equally well to stimulation with the immunogen or the r-fragment C of hornet Ag5 (residue 151-204).

Proliferation of Tpx-N or -C primed spleen cells was also tested on stimulation with synthetic peptides which correspond to sequences present in r-fragment IN and C of hornet Ag5. The data in FIG. 15 show high stimulation indices (greater than 6) for both r-fragments Tpx-N and fragment IN, only moderate stimulation indices (about 3) for peptides 7, 8 and 9, and near baseline stimulation indices of about 2 or less for the remaining peptides. The data in FIG. 16 show high stimulation indices (greater than 15) for Tpx-C, 9 for fragment C, 6 for peptide 18, and 2 or less for all other peptides.

The data in FIGS. 15 and 16 were obtained from mice after 4 immunizations. Further studies after five immunizations are planned as the data in FIGS. 7 to 10 indicate that stronger stimulation indices are obtained after longer immunization.

Discussion

The present Example defines indices of 4 or greater for proliferation of Ag5- specific cells as containing a T cell epitope of Ag5. With this definition, the data in FIGS. 3–13 for mice of 5 strains with different haplotypes would indicate that the T cell epitopes of Ag5 are distributed throughout the entire molecule. This is summarized in Table 4. As C57B1/6 mice is a poor responder, its data are excluded in the following comparison.

The data in Table 4 indicate that 14 peptides contain T cell epitopes of Ag5. Three of these peptides are recognized by three of the four strains tested, five of them by two strains and the remaining six by only one strain. The peptides which are recognized by two or three strains of mice are indicated in bold face characters in Table 2. They are peptides 1, 2, 5, 6, 9, 15, 20 and 18. As can be seen in FIG. 1, there are extensive sequence identities of these white faced hornet peptides with those of the other vespids. This is particularly apparent for peptides 6, 20, and 18.

In addition to the seven vespid Ag5 sequences in FIG. 1, there are eight other vespid Ag5s with known sequences. They are nearly identical to those in FIG. 1, depending on their species group [Lu, et al., *J. Immunol.*, 150:2823–2830 (1993); Hoffman, *J. Allergy Clin. Immunol.*, 92:707–716 (1993)]. Fire ant venom allergen Sol i 3 also has sequence similarity with vespid Ag5s [Hoffman, *J. Allergy Clin. Immunol.*, 91:71–78 (1993)]. Peptides 9, 20 and 18 of white faced hornet Ag5 have a high degree of sequence identity with the corresponding peptides of Sol i 3.

It is most likely that these vespid and fire ant Ag5s have T cell epitopes of identical and/or similar sequences. These epitopes studies are being continued with yellowjacket or paper wasp Ag5 immunized mice.

The finding of cross reactive T cell epitopes of hornet Ag5 and a mammalian testis protein is interesting, although its significance in clinical allergy, if any, is unknown. Published reports do not indicate any unusual distribution of male and female insect allergic patients. Our own unpublished studies showed that male and female BALB/c mice gave indisguisable antibody response when immunized with hornet Ag5 in presence of alum.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

What is claimed is:

1. A method for treating sensitivity to vespid venom antigen 5 comprising administering to a vespid venom allergic patient a therapeutically effective amount of a peptide characterized by the following properties:

a) it has a range of about 8 to about 35 amino acid residues of vespid venom antigen 5; and,
   b) it is antigenic for T cell proliferation in a mouse immunized with a vespid venom antigen 5, which mouse is a strain selected from the group consisting of BALB/c, ASW/Sn, C3H/He, and P/J.

2. The method according to claim 1, wherein the peptide corresponds to a fragment of white face hornet antigen 5, form 2, having an amino acid sequence selected form the group consisting of:

| | |
|---|---|
| NNYCKIKCRKGIHTLCKFGT; | (SEQ ID NO:8) |
| GIHTLCKFGTSMKPNCGRNV; | (SEQ ID NO:9) |
| KNEILKRHNDFRQNVAKGLE; | (SEQ ID NO:12) |
| FRQNVAKGLETRGKPGPQPP; | (SEQ ID NO:13) |
| TRGKPGPQPPAKNMNVLVWN; | (SEQ ID NO:14) |
| DELAKIAQTWANQCDFNHDD; | (SEQ ID NO:16) |
| CRNTAKYQVGQNIAISSTTA; | (SEQ ID NO:18) |
| QNIAISSTTATQFDRPSKLI; | (SEQ ID NO:19) |
| TQFDRPSKLIKQWEDEVTEF; | (SEQ ID NO:20) |
| KQWEDEVTEFNYKVGLQNSN; | (SEQ ID NO:21) |
| NYKVGLQNSNFRKVGHYTQM; | (SEQ ID NO:22) |
| FRKVGHYTQMVWGKT; | (SEQ ID NO:23) |
| KEIGCGSIKYIEDNWYTHYL; and | (SEQ ID NO:25) |
| IEDNWYTHYLVCNYGPGGND. | (SEQ ID NO:26) |

3. The method according to claim 1, wherein the peptide has a sequence selected from the group consisting of:

| | |
|---|---|
| NNYCKIKCRKGIHTLCKFGT; | (SEQ ID NO:8) |
| GIHTLCKFGTSMKPNCGRNV; | (SEQ ID NO:9) |
| KNEILKRHNDFRQNVAKGLE; | (SEQ ID NO:12) |
| FRQNVAKGLETRGKPGPQPP; | (SEQ ID NO:13) |
| DELAKIAQTWANQCDFNHDD; | (SEQ ID NO:16) |
| NYKVGLQNSNFRKVGHYTQM; | (SEQ ID NO:22) |
| FRKVGHYTQMVWGKT; and | (SEQ ID NO:23) |
| IEDNWYTHYLVCNYGPGGND. | (SEQ ID NO:26) |

4. The method according to claim 1, wherein the patient has been identified as sensitive to vespid venom antigen 5.

5. The method according to claim 1, wherein the peptide is formulated in a pharmaceutical composition.

6. A method for treating sensitivity to vespid venom antigen 5 comprising administering to a vespid venom allergic patient a therapeutically effective amount of a peptide having an amino acid sequence selected from the group consisting of:
 a) NNYCKIKCRKGIHTLCKFGT (SEQ ID NO:8), or its homolog;
 b) GIHTLCKFGTSMKPNCGRNV (SEQ ID NO:9), or its homolog;
 c) NNYCKIKCRKGIHTLCKFGTGTSMKPNCGRNV (SEQ ID NO:42), or its homolog;
 d) KNEILKRHNDFRQNVAKGLE (SEQ ID NO: 12), or its homolog;
 e) FRQNVAKGLETRGKPGPQPP (SEQ ID NO: 13), or its homolog;
 f) KNEILKRHNDFRQNVAKGLETRGKPGPQPP (SEQ ID NO:43), or its homolog;
 g) DELAKIAQTWANQCDFNHDD (SEQ ID NO:16), or its homolog;
 h) NYKVGLQNSNFRKVGHYTQM (SEQ ID NO:22), or its homolog;
 i) FRKVGHYTQMVWGKT (SEQ ID NO.23), or its homolog;
 j) NYKVGLQNSNFRKVGHYTQMVWGKT (SEQ ID NO:44), or its homolog;
 k) IEDNWYTHYLVCNYGPGGND (SEQ ID NO:26), or its homolog.

7. The method according, to claim 6, wherein the patient has been identified as sensitive to vespid venom antigen 5.

8. The method according to claim 6, wherein the peptide is formulated in a pharmaceutical composition.

9. A method for treating sensitivity to vespid venom antigen 5 comprising administering to a vespid venom allergic patient a therapeutically effective amount of a recombinant polypeptide comprising two or more peptides non-contiguously arranged relative to the native sequence of vespid venom antigen 5, wherein the peptides are selected from the group consisting of:
 a) NNYCKIKRKGIHTLCKFGT (SEQ ID NO:8), or its homolog;
 b) GIHTLCKFGTSMKPNCGRNV (SEQ ID NO:9), or its homolog;
 c) NNYCKIKCRKGIHTLCKFGTGTSMKPNCGRNV (SEQ ID NO:42), or its homolog;
 d) KNEILKRHNDFRQNVAKGLE (SEQ ID NO:12), or its homolog;
 e) FRQNVAKGLETRGKPGPQPP (SEQ ID NO:13), or its homolog;
 f) KNEILKRHNDFRQNVAKGLETRGKPGPQPP (SEQ ID NO:43), or its homolog;
 g) DELAKIAQTWANQCDFNHDD (SEQ ID NO:16), or its homolog;
 h) NYKVGLQNSNFRKVGHYTQM (SEQ ID NO:22), or its homolog;
 i) FRKVGHYTQMVWGKT (SEQ ID NO:23), or its homolog;
 j) NYKVGLQNSNFRKVGHYTQMVWGKT (SEQ ID NO:44), or its homolog; and,
 k) IEDNWYTHYLVCNYGPGGND (SEQ ID NO:26), or its homolog.

10. The method according to claim 9, wherein the patient has been identified as sensitive to vespid venom antigen 5.

11. The method according to claim 9, wherein the peptide is formulated in a pharmaceutical composition.

* * * * *